(12) United States Patent
Rabinovich et al.

(10) Patent No.: US 8,859,229 B2
(45) Date of Patent: Oct. 14, 2014

(54) TRANSIENT TRANSFECTION WITH RNA

(75) Inventors: Peter M. Rabinovich, Madison, CT (US); Sherman M. Weissman, Milford, CT (US); Marina E. Komarovskaya, Milford, CT (US); Erkut Bahceci, Hamden, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 12/025,700

(22) Filed: Feb. 4, 2008

(65) Prior Publication Data

US 2008/0260706 A1 Oct. 23, 2008

Related U.S. Application Data

(60) Provisional application No. 60/899,144, filed on Feb. 2, 2007.

(51) Int. Cl.
| | | |
|---|---|---|
| C12P 21/06 | (2006.01) |
| C12N 15/85 | (2006.01) |
| C12P 21/04 | (2006.01) |
| C12P 19/34 | (2006.01) |
| C12N 15/64 | (2006.01) |
| C07H 21/00 | (2006.01) |
| C07H 21/02 | (2006.01) |
| C07H 21/04 | (2006.01) |

(52) U.S. Cl.
CPC ..................... C12N 15/85 (2013.01)
USPC ....... 435/69.1; 435/70.1; 435/70.3; 435/91.1; 435/91.3; 435/91.4; 435/91.42; 536/22.1; 536/23.1; 536/24.1; 536/24.2

(58) Field of Classification Search
None
See application file for complete search history.

(56) References Cited

U.S. PATENT DOCUMENTS

| | | | |
|---|---|---|---|
| 4,394,448 A | 7/1983 | Szoka et al. | |
| 4,619,794 A | 10/1986 | Hauser | |
| 4,946,778 A | 8/1990 | Ladner | |
| 5,091,513 A | 2/1992 | Huston | |
| 5,250,431 A | 10/1993 | Rudd | |
| 5,256,555 A * | 10/1993 | Milburn et al. | 435/195 |
| 5,359,046 A | 10/1994 | Capon | |
| 5,686,281 A | 11/1997 | Roberts | |
| 5,712,149 A | 1/1998 | Roberts | |
| 5,747,292 A | 5/1998 | Greenberg | |
| 5,807,707 A | 9/1998 | Andrews | |
| 5,837,693 A | 11/1998 | German et al. | |
| 5,840,304 A | 11/1998 | Davis | |
| 5,858,740 A | 1/1999 | Finer | |
| 5,861,314 A | 1/1999 | Philip | |
| 5,912,172 A | 6/1999 | Eshhar | |
| 6,103,521 A | 8/2000 | Capon | |
| 6,355,476 B1 | 3/2002 | Kwon | |
| 6,407,221 B1 | 6/2002 | Capon | |
| 6,410,319 B1 | 6/2002 | Raubitschek | |
| 6,825,325 B1 | 11/2004 | Fischer | |
| 7,049,136 B2 | 5/2006 | Seed | |
| 7,070,995 B2 | 7/2006 | Jensen | |
| 7,323,553 B2 | 1/2008 | Fahrner | |
| 7,435,596 B2 | 10/2008 | Campana | |
| 7,446,179 B2 | 11/2008 | Jensen | |
| 7,466,179 B2 | 12/2008 | Huang | |
| 7,514,537 B2 | 4/2009 | Jensen | |
| 8,026,097 B2 | 9/2011 | Campana | |
| 8,071,374 B2 | 12/2011 | Har-Noy | |
| 2002/0001841 A1 | 1/2002 | Kaltoft | |
| 2002/0018749 A1 | 2/2002 | Hudson | |
| 2003/0083272 A1 | 5/2003 | Wiederholt | |
| 2003/0087846 A1 | 5/2003 | Wolpert | |
| 2003/0148982 A1 | 8/2003 | Brenner | |
| 2004/0038886 A1 | 2/2004 | Finney | |
| 2004/0043401 A1 | 3/2004 | Sadelain | |
| 2004/0058445 A1 | 3/2004 | Ledbetter | |
| 2005/0113564 A1 | 5/2005 | Campana | |
| 2006/0029595 A1 | 2/2006 | Kwon | |
| 2006/0078994 A1 | 4/2006 | Healey et al. | |
| 2006/0127985 A1 | 6/2006 | Goodwin | |
| 2006/0188490 A1 | 8/2006 | Hoerr et al. | |
| 2008/0152586 A1 | 6/2008 | Hudson | |
| 2008/0260706 A1 | 10/2008 | Rabinovich | |

(Continued)

FOREIGN PATENT DOCUMENTS

| | | |
|---|---|---|
| WO | 0018958 | 9/1998 |
| WO | WO 99/14346 | 3/1999 |

(Continued)

OTHER PUBLICATIONS

Boczkowski et al., 2000, Cancer Research, 60: 1028-1034.*
Vlachakis et al., 2001, Development, 128: 1299-1312.*
Sasaki et al., 1999, Journal of Virology, 73: 1219-1226.*
Chan et al., "The kalilo linear senescence-inducing plasmid of Neurospora is an invertron and encodes DNA and RNA polymerases" 20 Current Genetics 225-237 (1991).*

(Continued)

*Primary Examiner* — Celine Qian
*Assistant Examiner* — Nancy J Leith
(74) *Attorney, Agent, or Firm* — Pabst Patent Group LLP

(57) ABSTRACT

A method of mRNA production for use in transfection is provided, that involves in vitro transcription of PCR generated templates. This RNA can efficiently transfect different kinds of cells. This approach results in increased efficiency (fidelity and productivity) of mRNA synthesis and is less time consuming because it does not require cloning, and also consequently eliminates the unwanted errors and effects related to RNA made on DNA templates obtained with cloning techniques. The results of transfection of RNAs demonstrate that RNA transfection can be very effective in cells that are exceedingly difficult to transfect efficiently with DNA constructs. The method can be used to deliver genes into cells not- or only poorly transfectable for DNA, in vitro and in vivo.

20 Claims, 13 Drawing Sheets

(56) References Cited

U.S. PATENT DOCUMENTS

| | | |
|---|---|---|
| 2008/0311078 A1 | 12/2008 | Gokarn |
| 2009/0136498 A1 | 5/2009 | Haurum |
| 2009/0191172 A1 | 7/2009 | Cooper |
| 2009/0196877 A1 | 8/2009 | Chen |
| 2009/0226404 A1 | 9/2009 | Schuler |
| 2009/0257991 A1 | 10/2009 | Li |
| 2009/0263421 A1 | 10/2009 | Spetz-Holmgren |
| 2011/0038836 A1 | 2/2011 | Cooper |
| 2011/0044939 A1 | 2/2011 | Feuerer |
| 2011/0059056 A1 | 3/2011 | Grawunder |
| 2011/0070219 A1 | 3/2011 | Seefeldt |
| 2011/0091936 A1 | 4/2011 | Gawlitzek |
| 2011/0104128 A1 | 5/2011 | Cooper |
| 2011/0110909 A1 | 5/2011 | Ildstad |
| 2011/0143436 A1 | 6/2011 | Dahl et al. |
| 2011/0287979 A1 | 11/2011 | Gurney |
| 2011/0300179 A1 | 12/2011 | Spetz-Holmgren |
| 2012/0134970 A1 | 5/2012 | Yang |

FOREIGN PATENT DOCUMENTS

| | | |
|---|---|---|
| WO | 0014257 | 3/2000 |
| WO | 2004065546 | 8/2004 |
| WO | 2008095141 | 8/2008 |
| WO | 2009077134 | 6/2009 |
| WO | 2009091826 | 7/2009 |

OTHER PUBLICATIONS

Barbour et al., "The Nucleotide Sequence of a Linear Plasmid of *Borrelia burgdorferi* Reveals Similarities to Those of Circular Plasmids of Other Prokaryotes" 178(22) Journal of Bacteriology 6635-6639 (1996).*

Santopietro et al., "Cloning and Nucleotide Sequence of a Linear DNA Plasmid from Xanthophyllomyces dendrorhous (Pfaffia rhodozyma)" 46(4) Folia Microbiologica 277-288 (2001).*

Karlock et al., "Mutations in the Yeast Mitochondrial RNA Polymerase Specificity Factor, Mtf1, Verify an Essential Role in Promoter Utilization" 277(31) The Journal of Biological Chemistry 28143-28149 (2002).*

Mochizuki et al., "The large linear plasmid pSLA2-L of *Streptomyces rochei* has an unusually condensed gene organization for secondary metabolism" 48(6) Molecular Microbiology 1501-1510 (2003).*

Le Dantec et al., "Genomic Sequence and Transcriptional Analysis of a 23-Kilobase Mycobacterial Linear Plasmid: Evicence for Horizontal Transfer and Identification of Plasmid Maintenance Systems" 183(7) Journal of Bacteriology 2157-2164 (2001).*

Mielke et al., "Stabilized, long-term expression of heterodimeric proteins from tricistronic mRNA" 254 Gene 1-8 (2000).*

Arnaud-Barbe, "Transcription of RNA templates by T7 RNA polymerase", *Nuc. Acids Res.*, 26(15):3550-4554 (1998).

Boczkowski, "Induction of tumor immunity and cytotoxic T lymphocyte responses using dendritic cells transfected with messenger RNA amplified from tumor cells", *Cancer Res.*, 60(4):1028-1034 (2001).

Bahceci, "Immunotherapy of B cell malignancies using transiently redirected cytotoxic T cells", *Blood*, 110(11)Part 1:808A (2007).

Chamberlin, "New RNA polymerase from *Escherichia coli* infected with bacteriophage T7", *Nature*, 228(5268):227-231 (1970).

Cheung, "Anti-idiotypic antibody facilitates scFv chimeric immune receptor gene transduction and clonal expansion of human lymphocytes for tumor therapy", *Hybridoma and Hybridomics*, 22(4):209-218 (2003).

Cougot, "Cap-tabolism", *Trends in Biochem. Sci*, 29(8):436-444 (2004).

Davanloo, "Cloning and expression of the gene for bacteriophage T7 RNA polymerase", *Proc. Natl. Acad. Sci. USA*, 81(7):2035-2039 (1984).

Dunn and Studier, "Complete nucleotide sequence of bacteriophage T7 DNA and the locations of T7 genetic elements", *J. Mol. Biol.*, 166(4):477-535 (1983).

Elango, "Optimized transfection of mRNA transcribed from a d(A/T)100 tail-containing vector", *Biochem. Biophys. Res. Comm.*, 330(3), 958-966 (2005).

Felgner and Ringold, "Cationic liposome-mediated transfection", *Nature*, 337(6205):387-388 (1989).

Holtkamp, "Modification of antigen-encoding RNA increases stability, translational efficacy, and T-cell stimulatory capacity of dendritic cells", *Blood*, 108(13):4009-4017 (2006).

Mihara "Chimeric receptors with 4-1BB signaling capacity provoke potent cytotoxicity against acute lymphoblastic leukemia", *Leukemia*,18(4):676-684 (2004).

Imai, "Genetic modification of primary natural killer cells overcomes inhibitory signals and induces specific killing of leukemic cells", *Blood*, 106(1):376-383 (2005).

Kiyama and Oishi, "In vitro transcription of a poly(dA) x poly(dT)-containing sequence is inhibited by interaction between the template and its transcripts", *Nucleic Acids Res.*, 24(22):4577-4583 (1996).

Kiyama, "Instability of plasmid DNA maintenance caused by transcription of poly(dT)-containing sequences in *Escherichia coli*", *Gene*, 150(1):57-61 (1994).

Kotani, "Improved methods of retroviral vector transduction and production for gene therapy", *Hum. Gene Ther.*, 5(1):19-28 (1994).

Kowolik, "CD28 costimulation provided through a CD19-specific chimeric antigen receptor enhances in vivo persistence and antitumor efficacy of adoptively transferred T cells", *Cancel Res.*, 66(22):10995-11004 (2006).

Lee, "Efficient autointegration of avian retrovirus DNA in vitro", *J. Virol.*, 64(12):5958-5965 (1990).

Liu, "Development and validation of a T7 based linear amplification for genomic DNA", *BMC Genomics*, 4(1):19 (2003).

MacDonald, "Termination and slippage by bacteriophage T7 RNA polymerase", *J. Mol. Biol.*, 232(4):1030-1047 (1993).

MacKett, "General method for production and selection of infectious vaccinia virus recombinants expressing foreign genes", *J. Virol.*, 49(3):857-864 (1984).

Nacheva and Berzal-Herranz, "Preventing nondesired RNA-primed RNA extension catalyzed by T7 RNA polymerase", *Eur. J. Biochem.*, 270(7):1458-1465 (2003).

Nair, et al., "Induction of primary carcinoembryonic antigen (CEA)-specific cytoxic T lymphocytes in vitro using human dendritic cells transfected with RNA", *Nature Biotechnology*, 16(4):364-369 (1998).

Nakano, "Efficient coupled transcription/translation from PCR template by a hollow-fiber membrane bioreactor", *Biotechnol. Bioeng.*, 64(2):194-199 (1999).

Nishikawa, "Nonviral vectors in the new millennium: delivery barriers in gene transfer", *Hum. Gene Ther.*, 12(8):861-870 (2001).

Pestova, "Molecular mechanisms of translation initiation in eukaryotes", *Proc. Natl. Acad. Sci.*, 98(13):7029-7036 (2001).

Rabinovich, "Synthetic messenger RNA as a tool for gene therapy", *Human Gene Therapy*, 17(10):1027-1035 (2006).

Saeboe-Larssen, "mRNA—based electrotransfection of human dendritic cells and induction of cytotoxic T lymphocyte responses against the telomerase catalytic subunit (hTERT)", *J. Imm. Methods*, 259(1-2):191-203 (2002).

Saltzman and Desai, "Drug delivery in the BME curricula", *Annals of Biomedical Engineering*, 34(2):270-275 (2006).

Schenborn and Mierendorf, "A novel transcription property of SP6 and T7 RNA polymerases: dependence on template structure", *Nuc Acids Res.*, 13(17):6223-6236 (1985).

Schultze, "Follicular lymphomas can be induced to present alloantigen efficiently: a conceptual model to improve their tumor immunogenicity", *Proc. Natl. Acad. Sci.*, 92(18):8200-8204 (1995).

Shiramizu, "Identification of a common clonal human immunodeficiency virus integration site in human immunodeficiency virus-associated lymphomas", *Cancer Res.*, 54(8):2069-2072 (1994).

Spratt, "The lognormal frequency distribution and human cancer", *J. Surgical Research*, 9(3):151-157 (1969).

Stepinski, "Synthesis and properties of mRNAs containing the novel "anti-reverse" cap analogs 7-methyl(3'-0-methyl)GpppG and 7-methyl (3'-deoxy)GpppG", *RNA*, 7(10):1486-1495 (2001).

(56) References Cited

OTHER PUBLICATIONS

Triana-Alonso, "Self-coded 3'-extension of run-off transcripts produces aberrant products during in vitro transcription with T7 RNA polymerase", *J. Biol. Chem.,* 270(11):6298-6307 (1995).
Verma and Somia, "Gene therapy—promises, problems and prospects", *Nature,* 389(6648):239-242 (1997).
Wolff, "Direct gene transfer into mouse muscle in vivo", *Science,* 247(4949 Pt 1):1465-1468 (1990).
Yamanaka, "Induction of pluripotent stem cells from mouse fibroblasts by four transcription factors", *Cell Prolif.,* 41(Suppl 1):51-56 (2008).
Yu, "Induced pluripotent stem cell lines derived from human somatic cells", *Science,* 318(5858)1917-1920 (2007).
Yu, "Structural and functional analysis of an mRNP complex that mediates the high stability of human beta-globin mRNA", *Molecular and Cellular Biology,* 21(17):5879-5888 (2001).
Collas, et al., "On the way to reprogramming cells to pluripotency using cell-free extracts", Reprod. BioMed Online, 12(6):762-70 (2006).
Djuric and Ellis, "Epigenetic of induced pluripotency, the seven-headed dragon", *Stem Cell Res. Therapy,* 1(3):1-6 (2010).
Fuke and Ohno, "Role of poly(A) tail as an identity element for mRNA nuclear export", *Nucl Acids Res.,* 36:1037-49 (2008).
Muhlrad and Parker, "Aberrant mRNAs with extended 3\ UTRs are substrates for rapid degradation by mRNA surveillance", RNA, 5:1299-1307 (1999).
Plath and Lowry, "Progress in understanding reprogramming to the induced pluripotent state", Nature Rev., 12:253-65 (2011).
Sullivan, et al., "Elucidating nuclear reprogramming mechanisms: taking a synergistic approach", Reprod BioMed Online,16(1):41-50 (2008).
Wahle, "Poly (A) tail length control is caused by termination of processive synthesis", J Biol Chem., 270:2800-8 (1995).
Yakubov, et al., "Reprogramming of human fibroblasts to pluripotent stem cells using mRNA of four transcription factors", Biochem Biophys Res Comm., 398:189-93 (2010).
Hanna, et al., "Direct reprogramming of terminally differentiated mature B lymphocytes to piuripotency", Cell, 133:250-65 (2008).
Nienhuis, et al., "Genotoxicity of retroviral integration in hematopoietic cells", Molecular Therapy, 13:1031-49 (2006).
Finney, et al., "Chimeric receptors providing both primary and costimulatory signaling in T cells from a single gene product", *J Immunol.,* 161:2791-7 (1998).
Gross, and Eshhar, "Endowing T cells with antibody specificity using chimeric T cell receptors", FASEB, 6:3370-8 (1992).
Leahy, "A structural view of CD4 and CD8", FASEB,9:17-25 (1995).
Mihara, et al., "Chimeric receptors with 4-1BB signaling capacity provoke potent cytotoxicity against acute lymphoblastic leukemia", Leukemia, 18:676-84 (2004).
Porter, et al., "Chimeric antigen receptor-modified T cells in chronic lymphoid leukemia", NEJM, 365(8):725-33 (2011).
Rabinovich, et al., "Chimeric receptor mRNA transfection as a tool to generate antineoplastic lymphocytes", Hum Gene Therapy, 20:51-61(2009).
Schwarz, et al., "ILA, the human 4-1BB homologue, is inducible in lymphoid and other cell lineages", Blood, 85(4):1043-52 (1995).
So, et al., "Immune regulation and control of regulatory T cells by OX40 and 4-1BB", Cytokine Growth Factor Rev., 198(3-4):253-62 (2008).
Wucherpfennig, et al., "Structural biology of the T-cell receptor: Insights into receptor assembly, ligand recognition, and initiation of signaling", Cold Spring Herb Perspect Biol.,2:a005140 1-14 (2010).

* cited by examiner (SEQ ID NO:3)

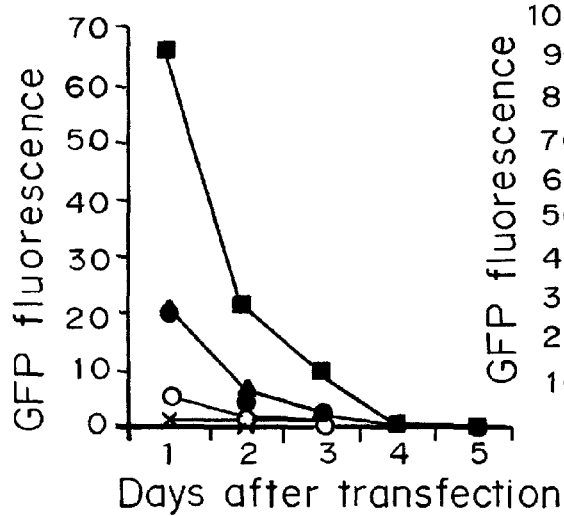
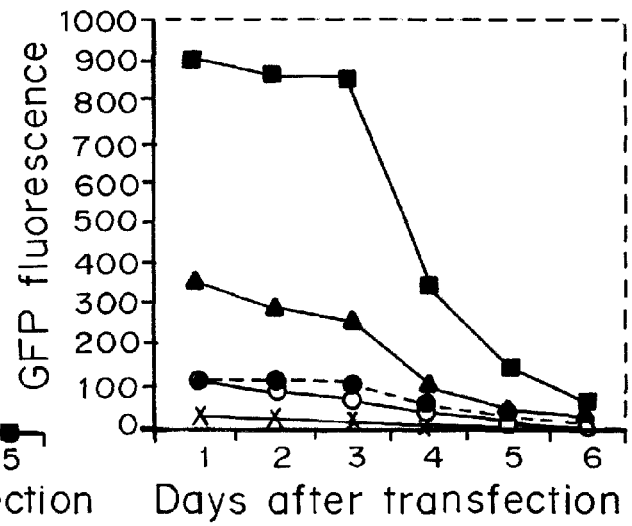
FIG. 3A    FIG. 3B
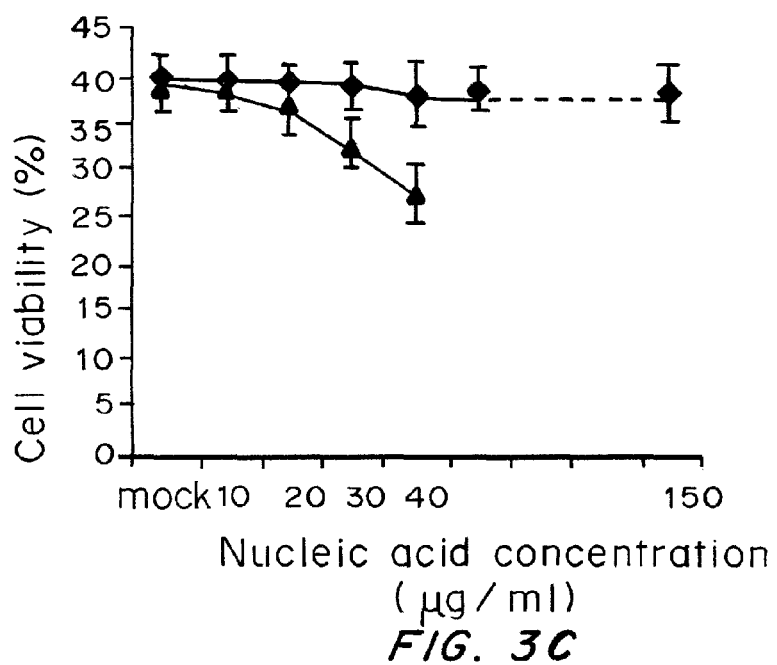
FIG. 3C

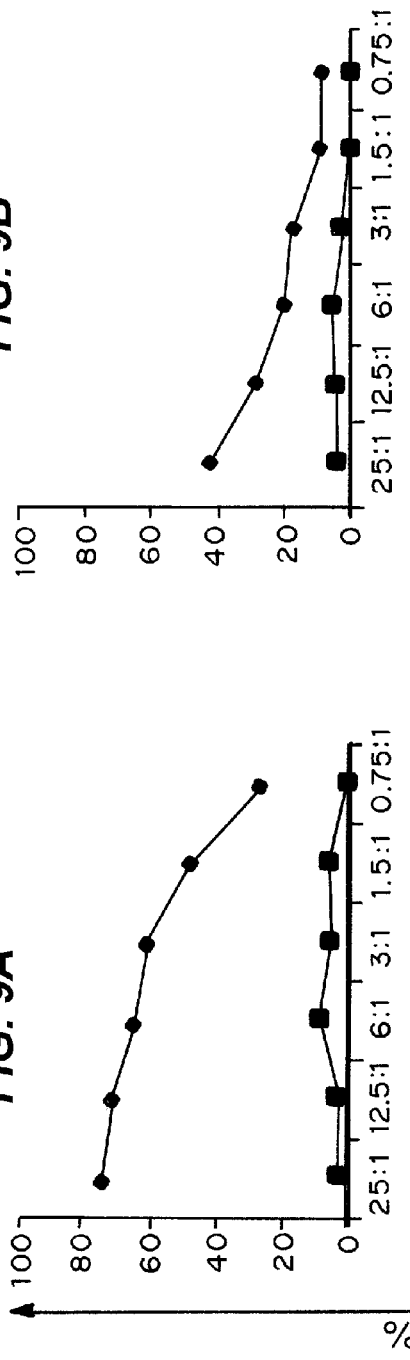
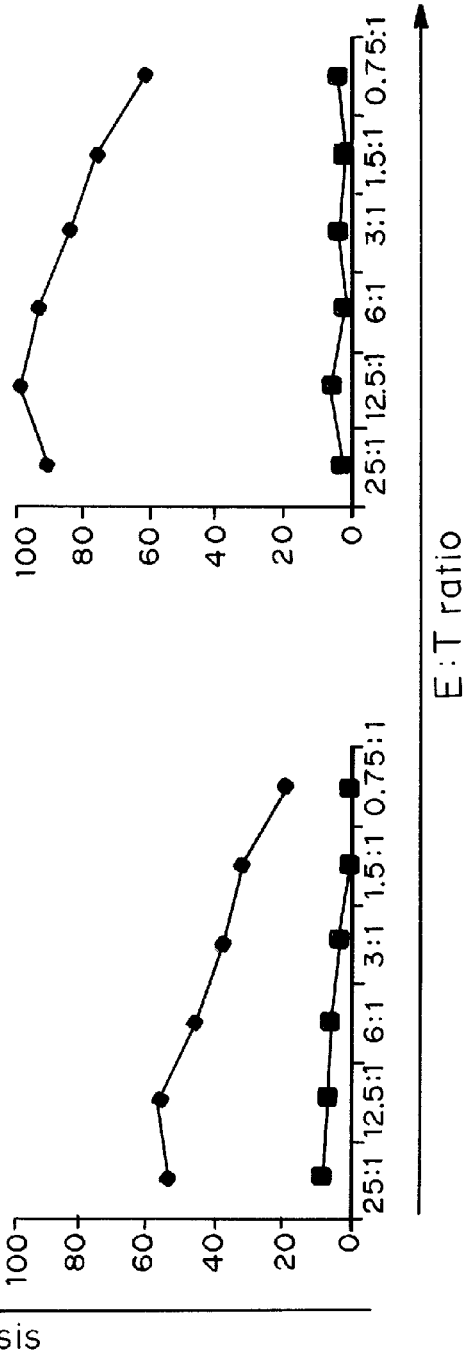
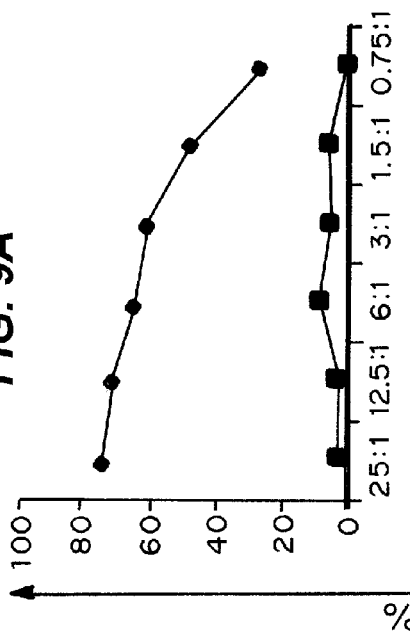
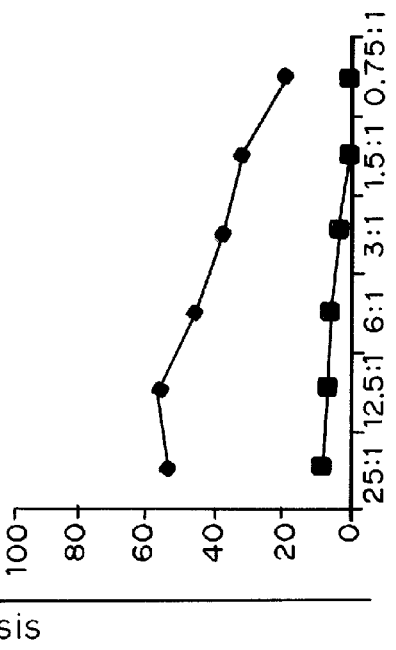
FIG. 9A
FIG. 9B
FIG. 9C
FIG. 9D

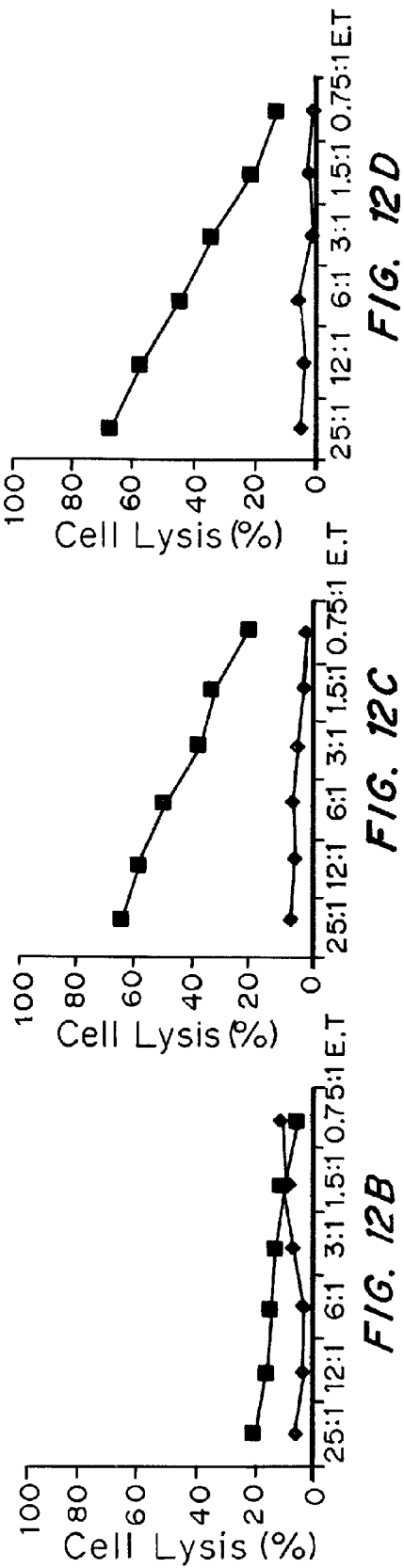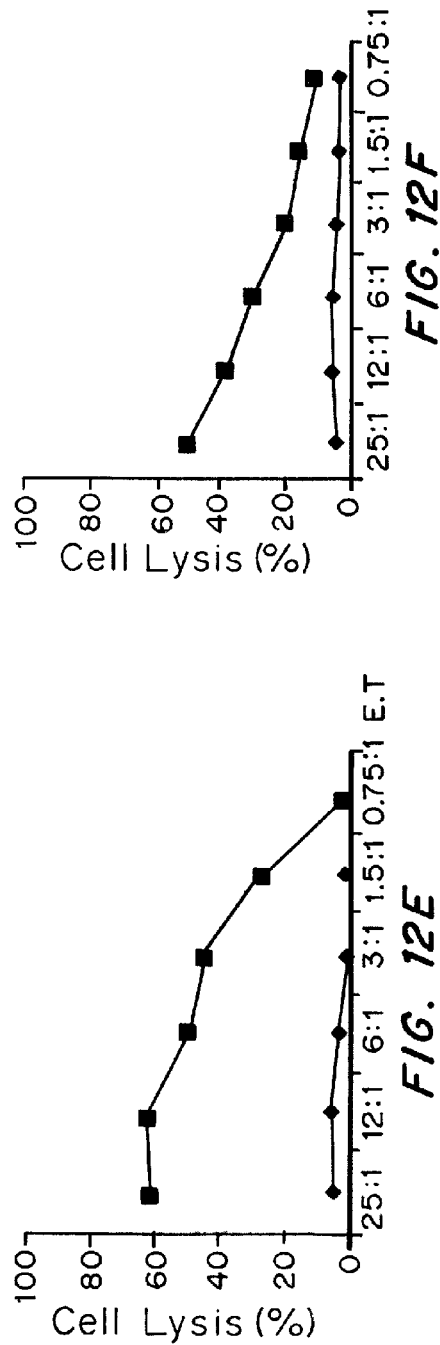

SEQUENCE LISTING

<160> NUMBER OF SEQ ID NOS: 3

<210> SEQ ID NO 1
<211> LENGTH: 8
<212> TYPE: RNA
<213> ORGANISM: Artificial Sequence
<220> FEATURE:
<223> OTHER INFORMATION: Synthetic poly Uridine

<400> SEQUENCE: 1

```
uuuuuuuu                                                              8

<210> SEQ ID NO 2
<211> LENGTH: 9
<212> TYPE: RNA
<213> ORGANISM: Artificial Sequence
<220> FEATURE:
<223> OTHER INFORMATION: Synthetic polyadenine

<400> SEQUENCE: 2 aaaaaaaaa                                                             9

<210> SEQ ID NO 3
<211> LENGTH: 14
<212> TYPE: RNA
<213> ORGANISM: Artificial Sequence
<220> FEATURE:
<223> OTHER INFORMATION: Synthetic poly A tail

<400> SEQUENCE: 3
aaaaaaaaaa aaaa                                                      14
```

TRANSIENT TRANSFECTION WITH RNA

GOVERNMENT RIGHTS

The United States government has certain rights in this invention by virtue of NIH grant numbers N01-HV-28186, AA15632, DA13334, AA11197, and AA000171.

CROSS-REFERENCE TO RELATED APPLICATIONS

This application claims priority to U.S. Ser. No. 60/899,144 filed Feb. 2, 2007.

FIELD OF THE INVENTION

The present invention is generally in the field of genetic engineering employing non-viral RNA-mediated gene delivery.

BACKGROUND OF THE INVENTION

The advent of recombinant DNA technology has led to substantial effort to develop methods to facilitate the transfection and transduction of therapeutic and other nucleic acid-based agents to specific cells and tissues. Known techniques provide for the delivery of such agents with a variety of genes, provided in recombinant expression constructs. These constructs are capable of mediating functionality of the genes once they arrive within a cell. Such developments have been critical to many forms of molecular medicine, specifically gene therapy, whereby a missing or defective gene can be replaced by an exogenous copy of the functional gene.

Introduction of foreign nucleic acid into a cell can be accomplished chemically, biologically, or mechanically. Some current methods include viral transduction and non-viral delivery, such as electroporation, lipid dependent, polymer dependent, polypeptide dependent delivery, calcium co-precipitation and transfection with "naked" DNA.

Viral approaches typically use a genetically engineered virus to infect a host cell, thereby "transducing" the cell with an exogenous nucleic acid. Among known viral vectors are recombinant viruses, poxviruses, herpes viruses, adenoviruses, and retroviruses. Such recombinants can carry heterologous genes under the control of promoters or enhancer elements, and are able to cause their expression in vector-infected host cells, as reviewed in Mackett et al., *J. Virol.* 49:3 (1994); Kotani et al., *Hum. Gene Ther.* 5:19-28 (1994). However, viral transfection approaches carry a risk of mutagenicity due to viral integration into the cellular genome, or as a result of undesirable viral propagation. Insertion of retroviral DNA can result in inactivation or ectopic activation of cellular genes, thereby causing diseases (Lee et al., *J. Virol.* 64:5958-5965 (1990)) or activation of oncogenes (Shiramizu et al., *Cancer Res.*, 54:2069-2072 (1994)). Furthermore, viral vectors also are susceptible to undesirable interactions with the host immune system.

Non-viral methods of gene delivery include such as electroporation, liposomal, polymer, polypeptide dependent delivery and transfection with "naked" DNA. Electroporation utilizes the application of brief, high-voltage electric pulses to a variety of animal and plant cells leads to the formation of pores and other disturbances in the plasma membrane (U.S. Pat. No. 4,394,448 to Szoka, Jr., et al. and U.S. Pat. No. 4,619,794 to Hauser). Nucleic acids can enter directly into the cell cytoplasm either through these as a consequence of the redistribution of membrane components that accompanies closure of the pores and membrane restoration. Liposomal and polypeptide dependent approaches mix the material to be transferred with lipids or non-toxic polymers to form particles able to penetrate cells and to deliver nucleic acisd into cytoplasm (Felgner and Ringold, *Nature*, 337:387-388 (1989), Saltzman and Desai, *Annals of Biomedical Engineering*, 34, 270-275 (2006).

Polypeptide dependent approaches involve the use of highly penetrating proteins and peptides mixed with a nucleic acid followed by exposure of a target cell to the nucleoprotein/nucleopeptide complex (Verma and Somia, *Nature*, 389: 239 (1997); Wolff et al., *Science*, 247:1465 (1990)). "Naked" DNA transfection approaches involve methods where nucleic acids are administered directly in vivo, for example, as described in U.S. Pat. No. 5,837,693 to German et al. In the "Naked" DNA approach, the nucleic acid is injected or otherwise contacted with the cells without any adjuvants.

A common disadvantage to known non-viral DNA delivery techniques is that the amount of exogenous protein expression produced relative to the amount of exogenous nucleic acid administered remains too low for most diagnostic or therapeutic procedures. Low levels of protein expression are often a result of a low rate of transfection of the nucleic acid and/or toxicity of exogenous DNA. In addition, some types of cells are very resistant to DNA transfection, and introduced foreign DNA can incorporate into the genome and act as a mutagen.

An alternative procedure for non-viral gene delivery is achieved by transfection of mRNA rather than DNA. In principle, unlike DNA transfection, introducing mRNA can have no permanent effect on the genetic structure of the cell, at least in the absence of rare reverse transcription events. There is limited literature on the application of mRNA transfection approaches (for example, Seaboe-Larssen, et al., *J. Imm. Methods*, 259:191-203 (2002); Boczkowski et al., *Cancer Res.*, 60:1028-1034 (2001); and Elango et al., *Biochem. Biophys. Res. Comm.*, 330, 958-966 (2005)), and little in the way of a systematic comparison of DNA and RNA transfection procedures. Most available literature for mRNA transfection is based on methods that involve labor intensive cloning the gene of interest in special vectors containing a bacteriophage upstream and polyA/T stretch downstream of the cloning site. Not only is cloning time consuming, but recombinant plasmids containing a stretch of poly(A/T) are often unstable in bacterial cells and prone to spontaneous mutations (Kiyama, et al., *Gene*, 150:1963-1969 (1994). Furthermore, most mRNAs that are generated from d(A/T)n vectors contain a short sequence of heterologous nucleotides following the poly(A) tail. The influence of these heterologous sequences on translation is unknown (Elango et al., *Biochem. Biophys. Res. Comm.*, 330, 958-966 (2005). There is therefore a need for a transfection method that circumvents the problems associated with vector-dependent transfection methods.

It is an object of the present invention to provide a more convenient and/or efficient method of mRNA production for transfection of different types of cells, including the types which are not transfectable for DNA.

It is also an object of the present invention to provide a method of mRNA transfection with minimal side effects and high efficiency, which allows transient expression of genes and desirable modification of cell phenotype without cause permanent genetic changes, which avoids risk associated with conventional gene therapy It is also an object of the present invention to provide a method of cell transfection with multiple genes wherein the level of each gene expression can be individually controlled.

It is also an object of the present invention to provide a method of transfection of primary mammalian cells, including human cells, and use those cells for therapy of cancer, autoimmune and infectious diseases.

It is another object of the present invention to provide a method of transient cell modification, which allows fast and safe generation of diverse differentiation states of cells of different cell types, including diverse stem cells from various tissues such as fibroblasts, hematopoietic, epithelial cells and others.

SUMMARY OF THE INVENTION

A method of mRNA production for use in transfection is provided, that involves in vitro transcription of PCR generated templates with specially designed primers, followed by polyA addition, to produce a construct containing 3' and 5' untranslated sequence ("UTR"), a 5' cap and/or Internal Ribosome Entry Site (IRES), the gene to be expressed, and a polyA tail, typically 50-2000 bases in length. This RNA can efficiently transfect different kinds of cells. This approach results in increased efficiency (fidelity and productivity) of mRNA synthesis and is less time consuming because it does not require cloning, and also consequently eliminates the unwanted errors and effects related to RNA made on DNA templates obtained with cloning techniques.

The results of transfection of RNAs obtained using this method demonstrate that RNA transfection can be very effective in cells that are exceedingly difficult to transfect efficiently with DNA constructs. Further, the levels of gene expression following mRNA transfection are consistent from cell to cell in an experiment and these levels can be controlled over a wide range simply by changing the amount of mRNA that is transfected, and without obvious cytotoxic effects due to the levels of RNA per se. Due to high efficiency the cells can be simultaneously transfected with multiple genetic constructs. The method can be used to deliver genes into cells not-or only poorly transfectable for DNA, in vitro and in vivo.

It was hypothesized that the presence of a polyT stretch at the 3' end of the DNA template during runoff transcription creates a terminator-like hairpin which can dissociate the RNA polymerase from the template.

Figure 2A:
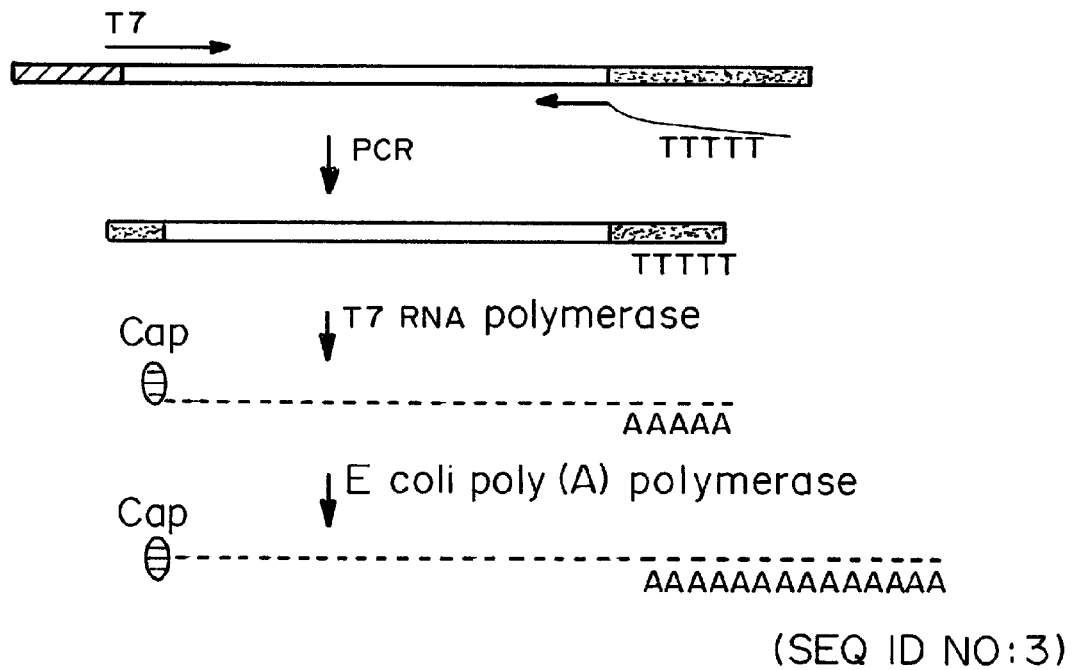

FIG. 2A shows a scheme for mRNA synthesis using a DNA template obtained by PCR with use of specially designed primers. The forward primer contains a bacteriophage promoter suitable for in vitro transcription and the reverse primer contains a polyT stretch. The PCR product is an expression cassette suitable for in vitro transcription. Polyadenylates on the 3' end of the nascent mRNA can prevent aberrant RNA runoff synthesis and creation of double strand RNA product.

After completion of transcription polyA tail can be additionally extended with poly(A) polymerase.

Figure 2B:
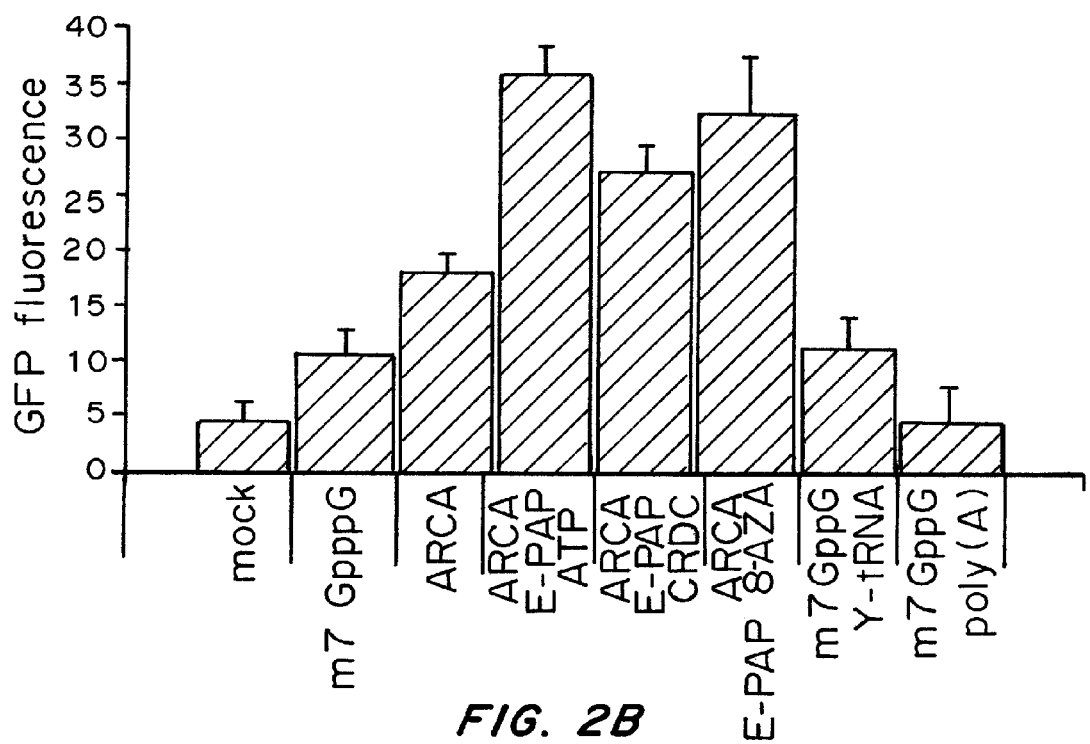

FIG. 2B shows the efficiency of mRNA transfection depending on its structure. EML cells were transfected with 60 μg/ml GFP mRNAs made with a standard cap analog dinucleotide or cap analog, 3-O-Methyl-m7G[5']ppp[5']G (ARCA). Certain transcripts were treated with E. coli Poly (A) polymerase in the presence of ATP, ATP analogs: cordycepin (CDCP) or 8-aza-adenosine (8-AZA). Certain transfections were performed in the presence of 1 mg/ml polyadenylate RNA or yeast tRNA. GFP expression was analyzed by FACS. The expression efficiency was calculated as the geometric mean of fluorescence intensity (+SD; n=3) as reported by the FACS instrument. Capping as well polyadenylation increased GFP expression. Incorporation of ATP analogs in the 3' end of the mRNA also increased expression, probably by protecting the 3' end from RNAse.

FIG. 3 shows the duration in days of GFP mRNA expression in Jurkat (FIG. 3B) and EML (FIG. 3A) cells. Cells transfected with 6 (-x-), 17 (-○-), 50 (-▲-) or 150 (-■-) mg/ml GFP mRNA or 10 mg/ml DNA (-●-) were analyzed by FACS during the duration of GFP expression. The expression efficiency was calculated as the difference between the geometric mean of fluorescence of the transfectants and control (mock transfected) cells. The fluorescence value of mock transfected cells was approximately 3 units (negative control). Therefore 63 and 603 units of total fluorescence correspond to 60 and 600 units increase of fluorescence above the control. FIG. 3c shows the viability of EML cells transfected with different levels of GFP plasmid DNA (-▲-) or mRNA (-♦-). Viability was calculated by Trypan Blue dye exclusion (Phelach, In: Current protocols in Cell biology, John Wiley & Sons, Inc., 2006). The mean percent (+SD; n=3) of the cells collected 18 h after transfection is shown.

Figure 4:
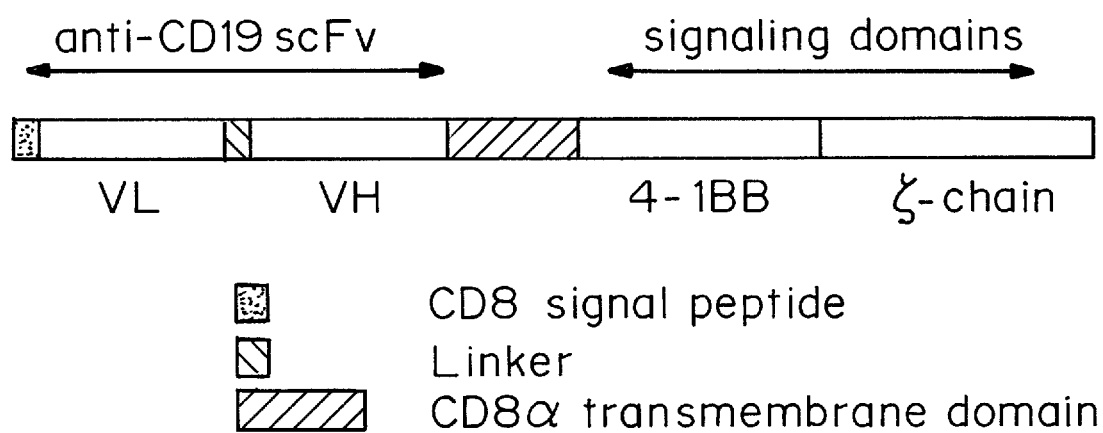

FIG. 4 is a schematic representation of the chimeric anti-CD19-CIR construct. $V_L$ and $V_H$—are extracellular single strand antibody domains, 4-1BB and ζ are intracellular signal domains.

Figure 5:
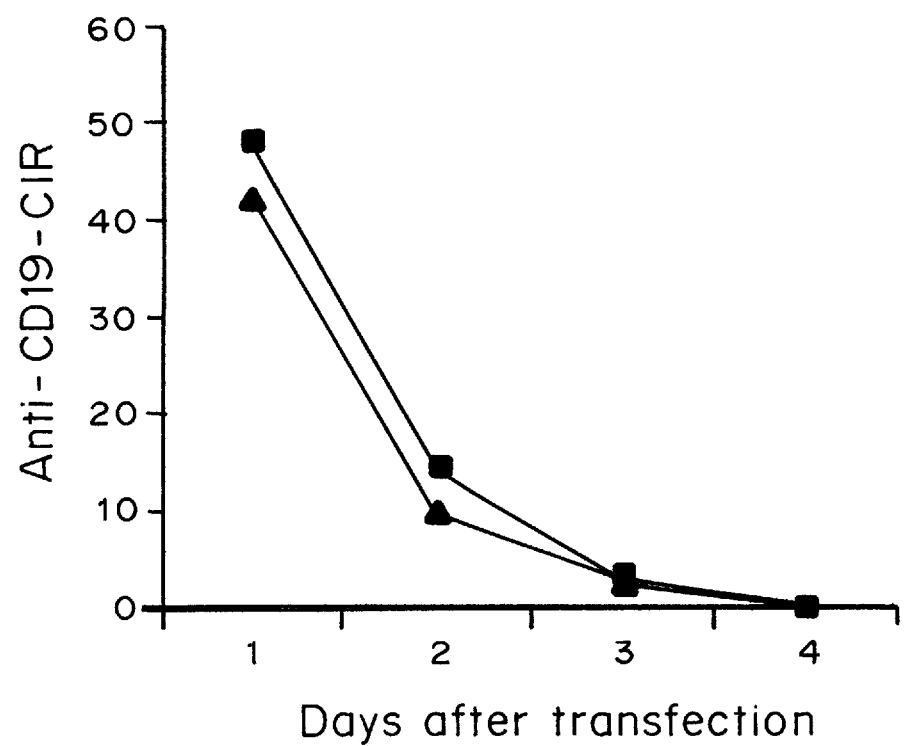

FIG. 5 shows transfection of $CD3^+$ T lymphocytes with anti-CD19-CIR mRNA. $CD4^+$ and $CD8^+$ cells were transfected with 40 μg/ml anti-CD19-CIR mRNA and analyzed by FACS during duration (days). Cells were labeled using antibody specific to anti-CD19-CIR, CD8 and CD4. Anti-CD19-CIR expression efficiency was calculated as the difference between the geometric mean of fluorescence of the transfectants and control (mock transfected) cells. The fluorescence value of mock transfected cells was measured as approximately 3 units (negative control). Therefore 63 units of total fluorescence corresponded to 60 units increase of fluorescence above the control.

Figure 6A:
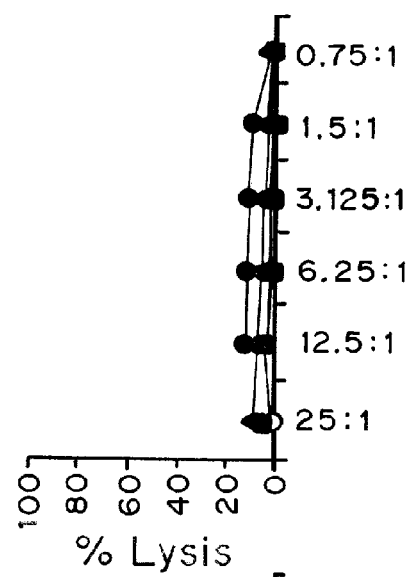
Figure 6B:
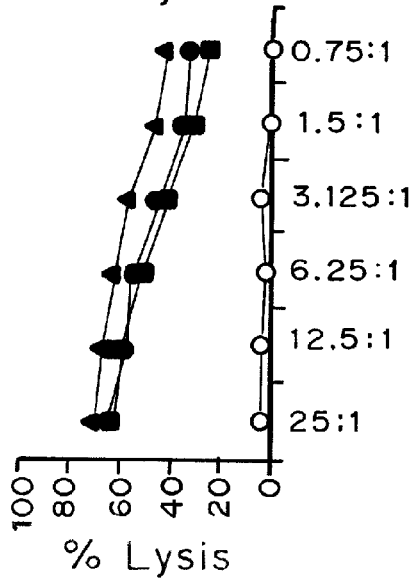
Figure 6C:
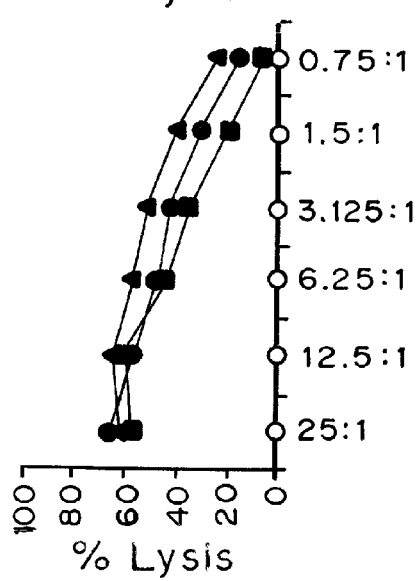
Figure 7A:
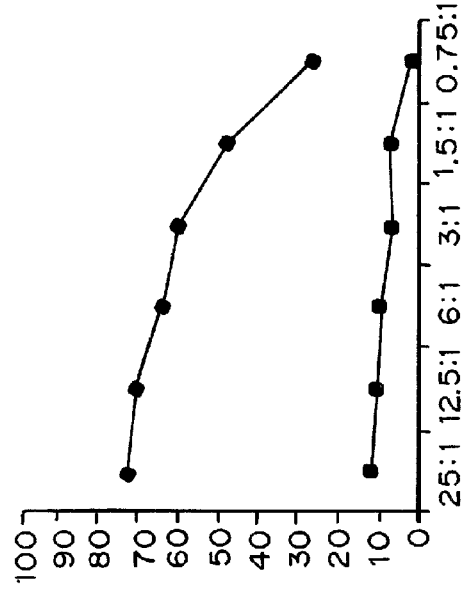
Figure 7B:
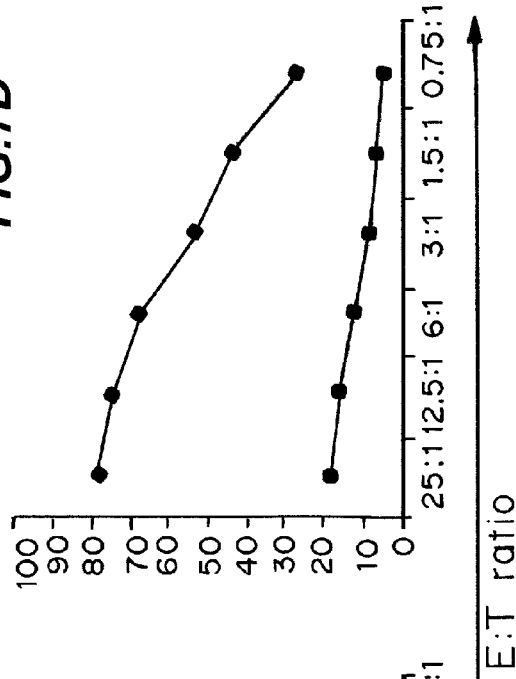
Figure 7C:
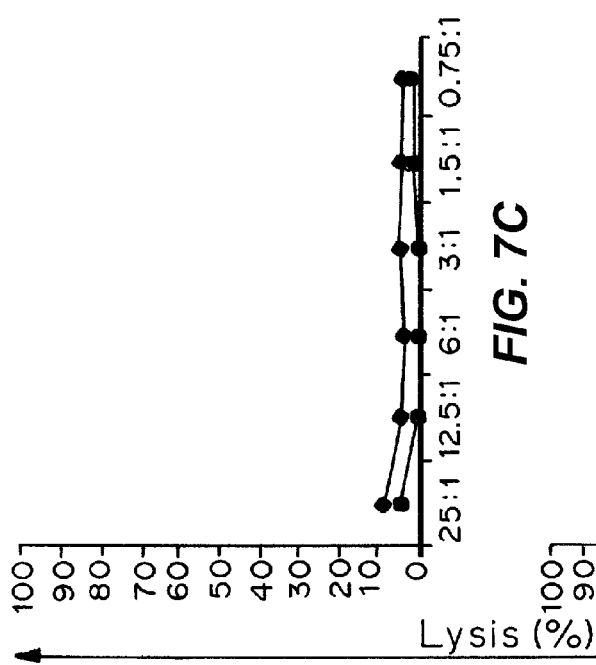
Figure 7D:
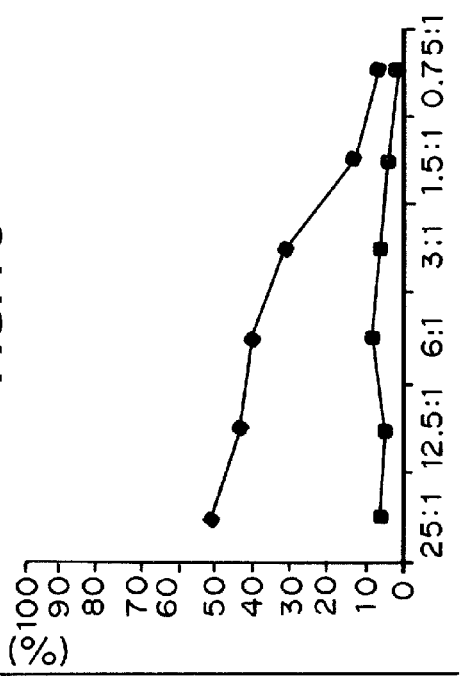

FIGS. 6A-C show cytotoxicity of CD8+ T lymphocytes (CTLs) transfected with various amounts of anti-CD19-CIR mRNA. CD8+ T lymphocytes were transfected with various amounts of anti-CD19-CIR mRNA. Cells were mock transfected (-○-) or transfected with anti-CD19-CIR mRNA at 13.3 μg/ml (-■-), 40 μg/ml (-▲-), or 120 μg/ml (-●-). The transfectants were analyzed for cytotoxicity with different targets at the indicated E:T ratio T lymphocytes were incubated for 4 hr with different target cells, loaded with $^{51}$Cr; FIG. 6A, autologous cells CD19+ B cells; FIG. 6B, allogeneic CD19+ B lymphoblasts; FIG. 6C, CD19 negative K562 cells.

FIGS. 7a-d show cytotoxicity of anti-CD19 CIR+ CTLs against CD19+ tumor cells. CTLs were mock transfected (-■-) or transfected with anti-CD19 CIR mRNA (-♦-). Target cells (K562-negative control, and other cells expressing CD19 antigen), were loaded with $^{51}$Cr and analyzed for cytotoxicity at the indicated E:T ratio. FIGS. 7A, 7B, 7C and 7D show the results for CD19 K562 cells, Daudi non-Hodgkin's lymphoma cells, autologous B cells, and NALM6 lymphoblastic leukemia cells, respectively.

Figure 8A:
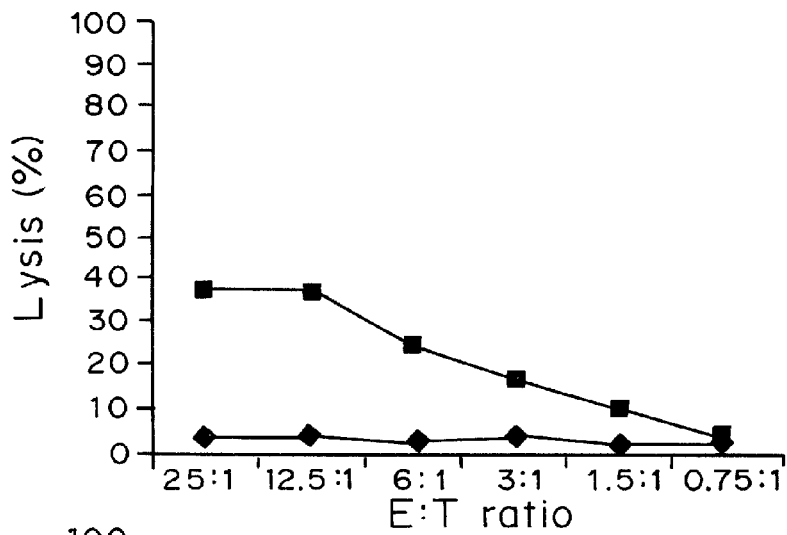
Figure 8B:
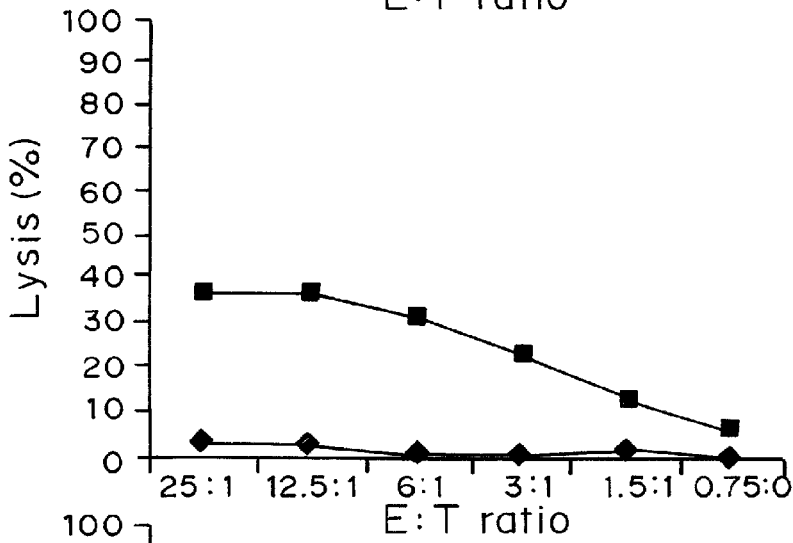
Figure 8C:
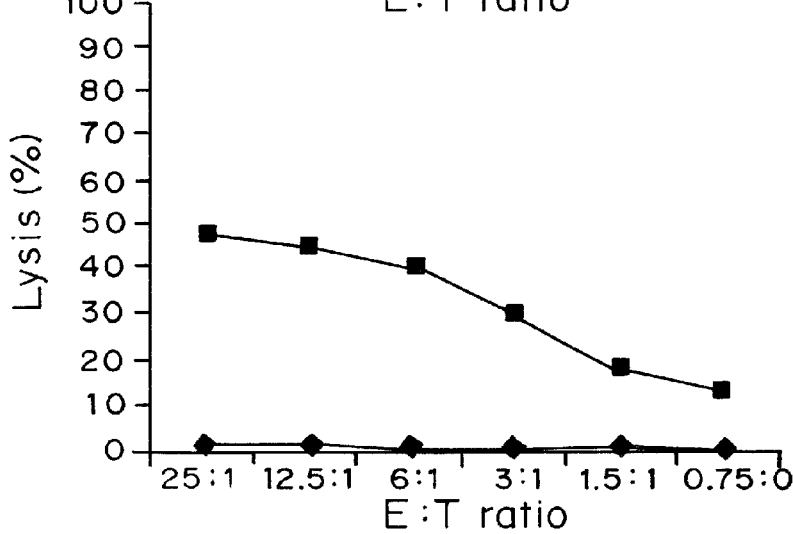

FIG. 8 shows CIR activity in different conditions. Cells were either mock transfected (-♦-) or transfected with anti-CD19 CIR (-■- in FIG. 8B) or anti-CD19 deltaCIR (-■- in FIG. 8C) mRNA. CTLs were activated for 1 day (FIG. 8A) or 7 days (FIGS. 8B and 8C) in the presence of CD3-CD28 beads and IL2. FIGS. 8A, 8B and 8C show the cytotoxicity (percent lysis) of transfected CTLs against autologous B cells at the indicated E:T ratios.

FIGS. 9A-D show the cytotoxicity of different lymphocyte subpopulations against autologous B cells. The different lymphocytes subpopulations were: $CD8^+$ (FIG. 9A), CD4+ T cells (FIG. 9B) and their (1:1) mix (FIG. 9C), and NK cells (FIG. 9D) transfected with anti-CD19 CIR mRNA (-♦-) or mock transfected (-■-). Targets, autologous CD19+ B cells, were loaded with $^{51}Cr$ and analyzed for cytotoxicity at the indicated E:T ratio.

Figure 10A:
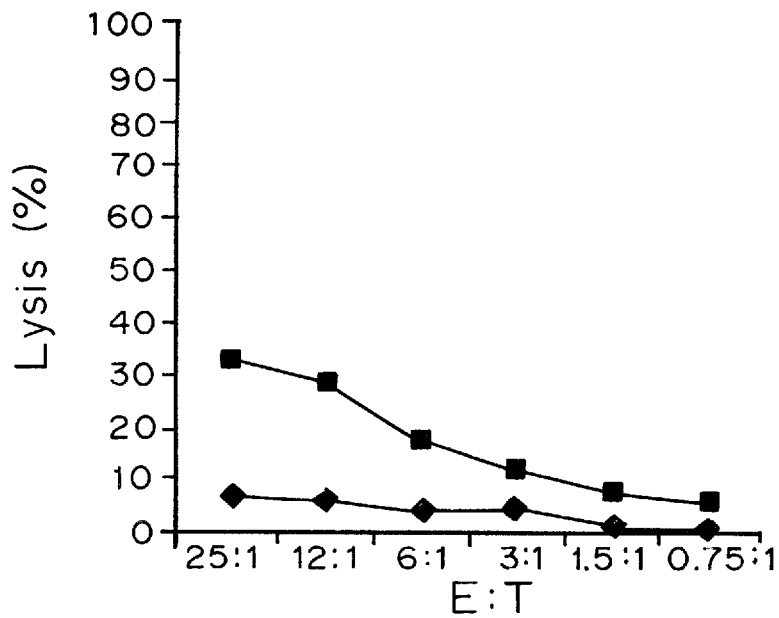
Figure 10B:
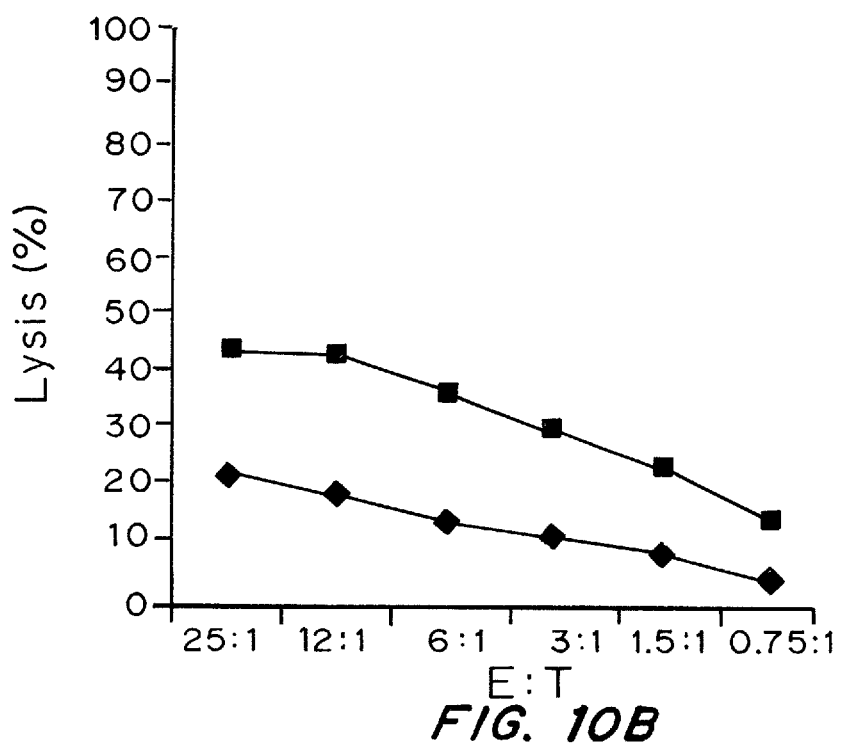

FIGS. 10A and 10B show cytotoxicity of mRNA-modified CTLs against mRNA-modified $CD19^-$ tumor cells. FIG. 10A shows cytotoxicity of CTLs transfected with anti-CD19 CIR mRNA against target K562 cells that were either mock transfected (-♦-) or transfected with CD19 receptor mRNA (-■-). FIG. 10B shows cytotoxicity of CTLs transfected with anti-CD19 CIR mRNA against target A2058 cells that were either mock transfected (-♦-) or transfected with CD19 receptor mRNA (-■-). It is shown that expression of CD19 receptor on both targets increased their sensitivity to CIR-mediated killing.

Figure 11:
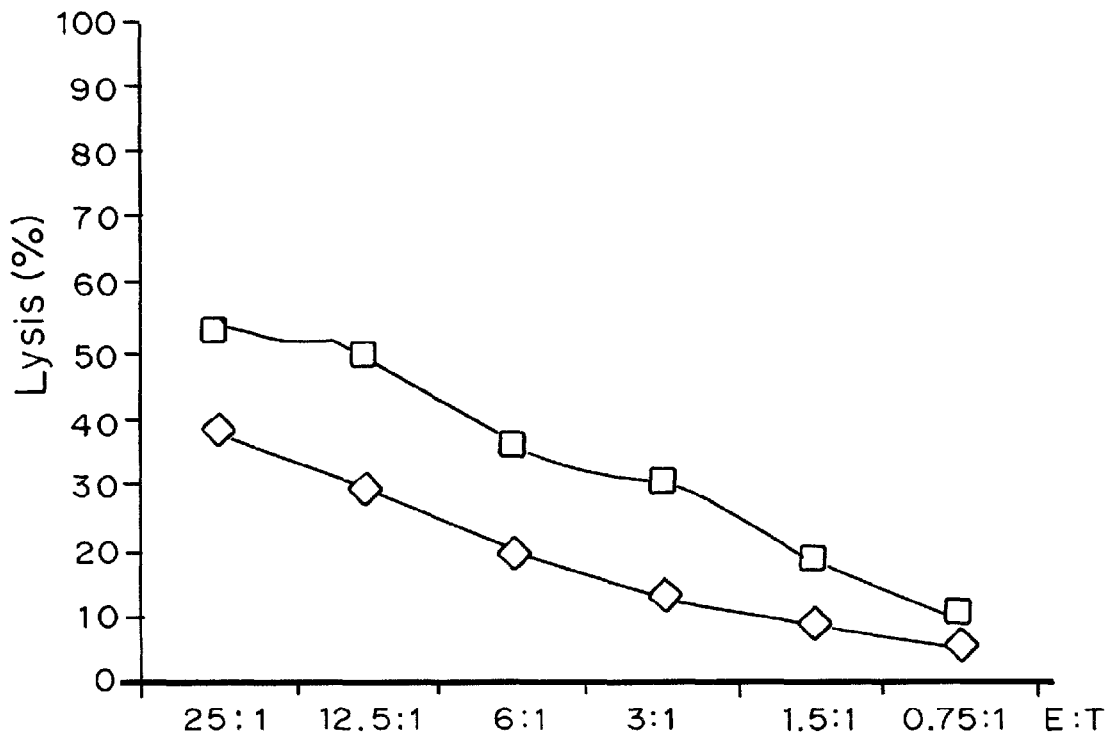

FIG. 11 shows cytotoxicity of mRNA-modified CTLs against mRNA-modified RPM18226 myeloma cells. RPM18226 myeloma cells that were either mock transfected (-◇-) or transfected with CD19 receptor mRNA (-□-) were loaded with $^{51}Cr$, mixed with anti-CD19 CIR+ CTLs and analyzed for cytotoxicity in the presence of anti-MHC1. Expression of CD19 receptor on myeloma cells increased their sensitivity to CIR-mediated killing.

Figure 12A:
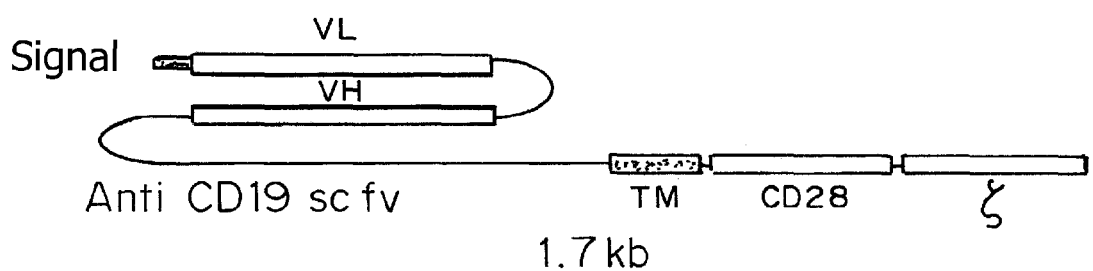

FIG. 12A shows the structure of 8H9 CIR, which can recognize gp58 antigen presented on various solid tumors (Cheung, et al. *Hybridoma and Hybridomics* 22(4):209-218 (2003). FIGS. 12B-12F show the cytotoxicity of 8H9 CIR+ CTLs against solid tumors. CTLs were mock transfected (-♦-) or transfected with 8H8 CIR mRNA (-■-). Target cells were K562 erythroleukemia cells (FIG. 12B), T470 breast ductal carcinoma cells (FIG. 12C), HTB82 rhabdosarcoma cells (FIG. 12D), primary melanoma cells (FIG. 12E) or MCF7 breast adenocarcinoma cells (FIG. 12F). Target cells (K562-negative control, and other cells expressing gp58 antigen), were loaded with $^{51}Cr$ and analyzed for cytotoxicity at the indicated E:T ratio.

Figure 13:
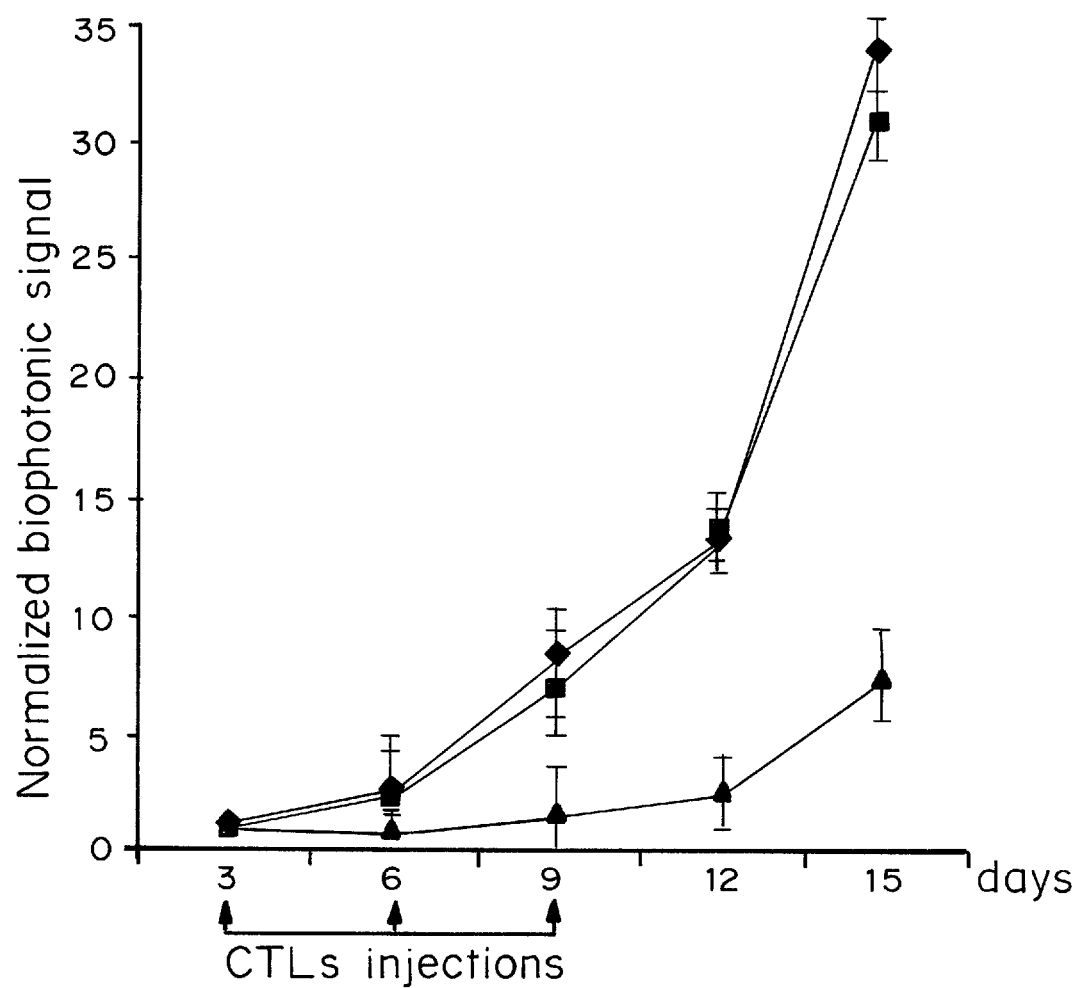

FIG. 13 shows the in vivo activity of anti-CD19 $CIR^+$ CTLs. 21 Nod-SCID mice were injected with $3\times10^6$ luciferase (ffLux) expressing Daudi cells and developed exponentially growing tumors on day 3 after injection. These were imaged and divided into 3 groups: treated with RPMI medium (-♦-), mock transfected (-■-) or anti-CD19 CIR transfected (-▲-) $CD8^+$ CTLs. Groups received injections of $5\times10^6$ CTLs on days 3, 6 and 9. The mice were imaged on days 3, 6, 9, 12 and 15. FIG. 13 is a line graph showing the longitudinal monitoring of the bioluminescent signals of ffLuc+ Daudi cells injected into groups of two NOD/scid mice. Points are the geometric mean photon flux (in p/s/cm2/sr), normalized against initial signal for each mouse; bars, geometric SD.

DETAILED DESCRIPTION OF THE INVENTION

I. Definitions

The brief life of an mRNA molecule begins with transcription and ultimately ends in degradation. During its life, an mRNA molecule may be processed, edited, and transported prior to translation. During transcription, RNA polymerase makes a copy of a gene from the DNA to mRNA as needed. Eukaryotic RNA polymerase associates with mRNA processing enzymes during transcription so that processing can proceed quickly after the start of transcription. The short-lived, unprocessed or partially processed, product is termed pre-mRNA; once completely processed, it is termed mature mRNA. Eukaryotic pre-mRNA, however, requires extensive processing.

As used herein, a 5' cap (also termed an RNA cap, an RNA 7-methylguanosine cap or an RNA $m^7G$ cap) is a modified guanine nucleotide that has been added to the "front" or 5' end of a eukaryotic messenger RNA shortly after the start of transcription. The 5' cap consists of a terminal group which is linked to the first transcribed nucleotide. Its presence is critical for recognition by the ribosome and protection from RNases. Cap addition is coupled to transcription, and occurs co-transcriptionally, such that each influences the other. Shortly after the start of transcription, the 5' end of the mRNA being synthesized is bound by a cap-synthesizing complex associated with RNA polymerase. This enzymatic complex catalyzes the chemical reactions that are required for mRNA capping. Synthesis proceeds as a multi-step biochemical reaction. The capping moiety can be modified to modulate functionality of mRNA such as its stability or efficiency of translation.

As used herein, "polyadenylation"[7] refers to the covalent linkage of a polyadenylyl moiety, or its modified variant, to a messenger RNA molecule. In eulcaryotic organisms, most messenger RNA (mRNA) molecules are polyadenylated at the 3' end. The 3' poly(A) tail is a long sequence of adenine nucleotides (often several hundred) added to the pre-mRNA through the action of an enzyme, polyadenylate polymerase. In higher eulcaryotes, the poly(A) tail is added onto transcripts that contain a specific sequence, the polyadenylation signal. The poly(A) tail and the protein bound to it aid in protecting mRNA from degradation by exonucleases. Polyadenylation is also important for transcription termination, export of the mRNA from the nucleus, and translation. Polyadenylation occurs in the nucleus immediately after transcription of DNA into RNA, but additionally can also occur later in the cytoplasm. After transcription has been terminated, the mRNA chain is cleaved through the action of an endonuclease complex associated with RNA polymerase. The cleavage site is usually characterized by the presence of the base sequence AAUAAA near the cleavage site. After the mRNA has been cleaved, adenosine residues are added to the free 3' end at the cleavage site.

Eukaryotic mRNA that has been processed and transported to the cytoplasm (i.e. mature mRNA) can then be translated by the ribosome. Translation may occur at ribosomes free-floating in the cytoplasm, or directed to the endoplasmic reticulum. After a certain amount of time, the message is degraded by RNases into its component nucleotides. The limited longevity of mRNA enables a cell to alter protein synthesis rapidly in response to its changing needs.

Different mRNAs within the same cell have distinct lifetimes. In bacterial cells, individual mRNAs can survive from seconds to more than an hour; in mammalian cells, mRNA lifetimes range from several minutes to days. The greater the stability of an mRNA, the more protein may be produced from that transcript. The presence of AU-rich motifs in some mammalian mRNAs tends to destabilize those transcripts through the action of cellular proteins that bind these motifs. Rapid mRNA degradation via AU-rich motifs is a critical mechanism for preventing the overproduction of potent cytokines such as tumor necrosis factor (TNF) and granulocyte-macrophage colony stimulating factor (GM-CSF). Base pairing with a small interfering RNA (siRNA) or microRNA (miRNA) can also accelerate mRNA degradation.

As used herein, "transient" refers to expression of a non-integrated transgene for a period of hours, days or weeks, wherein the period of time of expression is less than the period of time for expression of the gene if integrated into the genome or contained within a stable plasmid replicon in the host cell.

As used herein, a "T7 promoter site" is a sequence of nucleotides to which the T7 RNA polymerase, a DNA-dependent RNA polymerase originally isolated from T7 bacteriophage, described by Davanloo, et al., *Proc. Natl. Acad. Sci. USA*, 81:2035-39 (1984), binds with high specificity, as described by Chamberlin, et al., *Nature*, 228:227-231 (1970).

As used herein, a poly(A) is a series of adenosines attached by polyadenylation to the mRNA. In the preferred embodiment of a construct for transient expression, the polyA is between 50 and 5000, preferably greater than 64, more preferably greater than 100, most preferably greater than 300 or 400. poly(A) sequences can be modified chemically or enzymatically to modulate mRNA functionality such as localization, stability or efficiency of translation.

As used herein, an "open reading frame" or "ORF" is a series of nucleotides that contains a sequence of bases that could potentially encode a polypeptide or protein. An open reading frame is located between the start-code sequence (initiation codon or start codon) and the stop-codon sequence (termination codon).

II. Methods of Making mRNA for Use in Transient Transfection

Disclosed herein are methods for producing RNA for transient transfection. The RNA is produced by in vitro transcription using a polymerase chain reaction (PCR)-generated template.

A. Sources of DNA for PCR

DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA.

In one embodiment, the DNA to be used for PCR contains an open reading frame. The DNA can be from a naturally occurring DNA sequence from the genome of an organism. In one embodiment, the DNA is a full length gene of interest of a portion of a gene. The gene can include some or all of the 5' and/or 3' untranslated regions (UTRs). The gene can include exons and introns. In one embodiment, the DNA to be used for PCR is a human gene. In another embodiment, the DNA to be used for PCR is a human gene including the 5' and 3' UTRs. The DNA can alternatively be an artificial DNA sequence that is not normally expressed in a naturally occurring organism. An exemplary artificial DNA sequence is one that contains portions of genes that are ligated together to form an open reading frame that encodes a fusion protein. The portions of DNA that are ligated together can be from a single organism or from more than one organism.

Genes that can be used as sources of DNA for PCR include genes that encode polypeptides that provide a therapeutic or prophylactic effect to an organism or that can be used to diagnose a disease or disorder in an organism. Preferred genes are genes which are useful for a short term treatment, or where there are safety concerns regarding dosage or the expressed gene. For example, for treatment of cancer, autoimmune disorders, parasitic, viral, bacterial, fungal or other infections, the transgene(s) to be expressed may encode a polypeptide that functions as a ligand or receptor for cells of the immune system, or can function to stimulate or inhibit the immune system of an organism. It is not desirable to have prolonged ongoing stimulation of the immune system, nor necessary to produce changes which last after successful treatment, since this may then elicit a new problem. For treatment of an autoimmune disorder, it may be desirable to inhibit or suppress the immune system during a flare-up, but not long term, which could result in the patient becoming overly sensitive to an infection.

B. PCR to Produce Templates for In Vitro Transcription

PCR is used to generate a template for in vitro transcription of mRNA which is used for transfection. Methods for performing PCR are well known in the art. Primers for use in PCR are designed to have regions that are substantially complementary to regions of the DNA to be used as a template for the PCR. "Substantially complementary", as used herein, refers to sequences of nucleotides where a majority or all of the bases in the primer sequence are complementary, or one or more bases are non-complementary, or mismatched. Substantially complementary sequences are able to anneal or hybridize with the intended DNA target under annealing conditions used for PCR. The primers can be designed to be substantially complementary to any portion of the DNA template. For example, the primers can be designed to amplify the portion of a gene that is normally transcribed in cells (the open reading frame), including 5' and 3' UTRs. The primers can also be designed to amplify a portion of a gene that encodes a particular domain of interest. In one embodiment, the primers are designed to amplify the coding region of a human cDNA, including all or portions of the 5' and 3' UTRs. Primers useful for PCR are generated by synthetic methods that are well known in the art. "Forward primers" are primers that contain a region of nucleotides that are substantially complementary to nucleotides on the DNA template that are upstream of the DNA sequence that is to be amplified. "Upstream" is used herein to refer to a location 5, to the DNA sequence to be amplified relative to the coding strand. "Reverse primers" are primers that contain a region of nucleotides that are substantially complementary to a double-stranded DNA template that are downstream of the DNA sequence that is to be amplified. "Downstream" is used herein to refer to a location 3' to the DNA sequence to be amplified relative to the coding strand.

Any DNA polymerase useful for PCR can be used in the methods disclosed herein. The reagents and polymerase are commercially available from a number of sources.

1. Untranslated Regions

Chemical structures with the ability to promote stability and/or translation efficiency may also be used. The RNA preferably has 5' and 3' UTRs. The examples below demonstrate that inclusion of 44 base pairs of 5' UTR into the PCR template enabled greater translation efficiency of transcribed CFP RNA when compared to PCR templates containing only 6 base pairs of 5' UTR. The examples also demonstrate that the addition of 113 base pairs of 3, UTR enables greater translation efficiency of transcribed GFP RNA when compared to PCR templates containing only 11 base pairs of 3, UTR. In general, the length of the 3' UTR exceeds 100 nucleotides, and therefore 3' UTR longer then 100 nucleotides is preferred. In one embodiment the 3' UTR sequence is between 100 and 5000 nucleotides. The length of the 5' UTR is not as critical as the length of the 3' UTR and can be shorter. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be derived from an RNA virus whose RNA genome is stable in cells. In other embodiments various nucleotide analogues can be used in the 3' or 5' UTR to impede exonuclease degradation of the mRNA.

2. RNA Polymerase Promoter

To enable synthesis of RNA from a DNA template without the need for gene cloning, a promoter of transcription should be attached to the DNA template upstream of the sequence to be transcribed. Bacteriophage RNA polymerase promoter sequences can be attached to the St UTR by different genetic engineering methods, such as DNA ligation, or can be added to the forward primer (5') of the sequence that is substantially complementary to the target DNA. When a sequence that functions as a promoter for an RNA polymerase is added to 5' end of the forward primer, the RNA polymerase promoter becomes incorporated into the PCR product upstream of the open reading frame that is to be transcribed. In one preferred embodiment, the promoter is a T7 polymerase promoter, as described above. Other useful promoters include, but are not limited to, T3 and SP6 RNA polymerase promoters. Consensus nucleotide sequences for T7, T3 and SP6 promoters are known in the art.

3. Poly(A) Tail and 5' Cap

In a preferred embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

Figure 1:
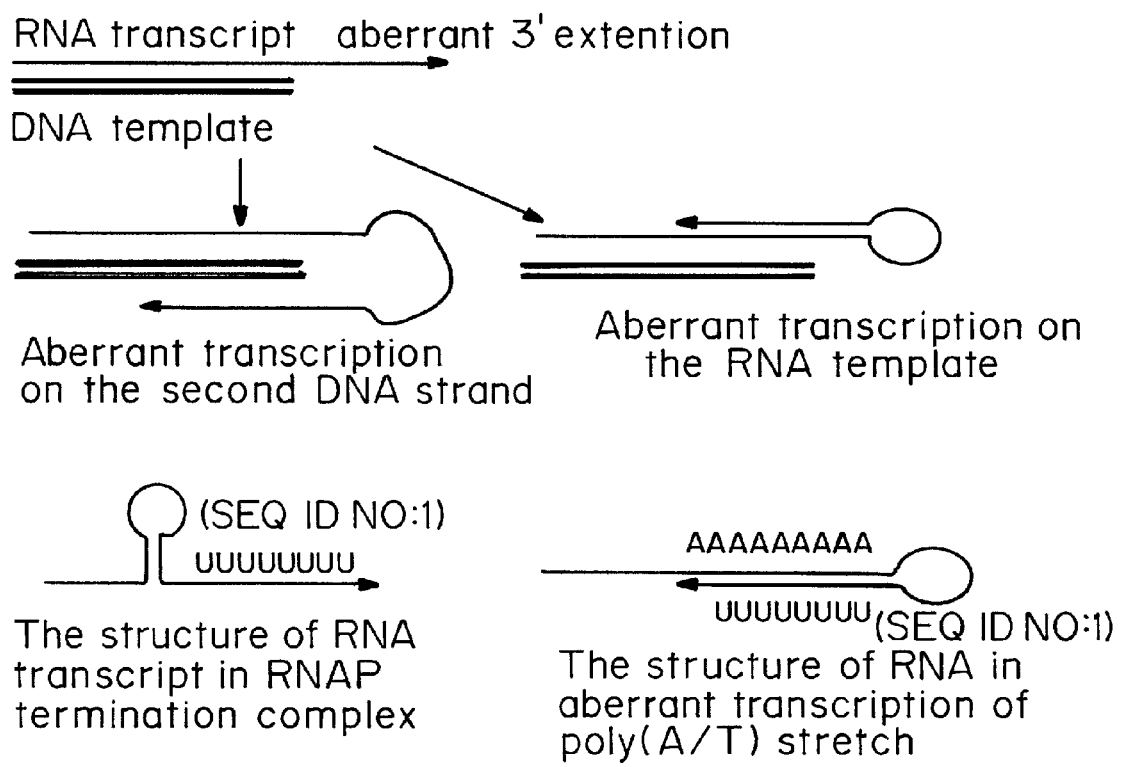
FIG. 1 shows a model of an aberrant T7 RNAP transcription in vitro, which explains why only those DNA templates which contain a polyA/T sequence are suitable for efficient transcription. On a linear DNA template, phage T7 RNA polymerase can extend the 3' end of the transcript beyond the last base of the template This could lead to runoff transcript bending followed by template exchange with the second DNA strand or transcription of RNA itself, and then to the aberrant transcription in a reverse direction and accumulation of double stranded RNA, which can inhibit gene expression. DNA linearization itself was not sufficient for correct transcription (Triana-Alonso et al., 1995; Dunn and Studier 1983; Arnaud-Barbe et al., 1998; Macdonald et al., 1993; Nakano et al., 1999).

On a linear DNA template, phage T7 RNA polymerase can extend the 3' end of the transcript beyond the last base of the template (Schenborn and Mierendorf, *Nuc Acids Res.*, 13:6223-36 (1985); Nacheva and Berzal-Herranz, *Eur. J. Biochem.*, 270:1485-65 (2003). This could lead to runoff transcript bending followed by template exchange with the second DNA strand or transcription of RNA itself (Triana-Alonso et al., *J. Biol. Chem.*, 270:6298-307 (1995); Dunn and Studier, *J. Mol. Biol.*, 166:477-535 (1983); Arnaud-Barbe et al., *Nuc. Acids Res.*, 26:3550-54 (1998); Macdonald et al., 1993), and then to the aberrant transcription in a reverse direction and accumulation of double stranded RNA, which can inhibit gene expression. DNA linearization itself is not sufficient for correct transcription (Triana-Alonso et al., *J. Biol. Chem.*, 270:6298-307 (1995); Dunn and Studier, *J. Mol. Biol.*, 166:477-535 (1983); Arnaud-Barbe et al., 1998 *Nuc. Acids Res.*, 26:3550-54 (1998); Macdonald et al., *J. Mol. Biol.*, 232:1030-47 (1993); Nakano et al., *Biotechnol. Bioeng.*, 64:194-99 (1999), plasmid DNA linearized downstream of a poly(A/T) stretch of 64-100 nucleotides results in good templates (Saeboe-Larssen et al., *J. Immunol. Meth.*, 259:191-203 (2002); Boczkowski et al., *Cancer Res.*, 60:1028-34 (2000); Elango et al., *Biochem Riophys Res Commun.*, 330:958-966 2005). An endogenous termination signal for T7 RNA polymerase encodes an RNA that can fold into a stem-loop structure followed by a track of uridine residues (Dunn and Studier, *J. Mol. Biol.*, 166:477-535 (1983); Arnaud-Barbe et al., 1998 *Nuc. Acids Res.*, 26:3550-54 (1998)). Even without a hairpin, a track of synthesized uridines can attenuate transcription (Kiyama and Oishi, *Nucleic Acids Res.*, 24:4577-4583 (1996). It was hypothesized that the linearization of plasmid DNA downstream of the poly(A/T) stretch probably formed a type of "dynamic" terminator preventing potential aberrant transcription: a 3' extension of the RNA transcript over a poly(A/T) stretch and transcription in the reverse direction will create a growing termination-like signal—an extended poly(U) stretch and a poly(A/U) hairpin (FIG. 1). Based on this presumption, reversed PCR primers were designed with a 3' anchoring sequence downstream of the GFP gene and a 5' 100 base stretch of poly(T) (FIG. 2A).

The conventional method of integration of polyA/T stretches into a DNA template is molecular cloning. However polyA/T sequence integrated into plasmid DNA can cause plasmid instability, which is why plasmid DNA templates obtained from bacterial cells are often highly contaminated with deletions and other aberrations. This makes cloning procedures not only laborious and time consuming but often not reliable. That is why a method which allows construction of DNA templates with polyA/T 3' stretch without cloning highly desirable.

The polyA/T segment of the transcriptional DNA template can be produced during PCR by using a reverse primer containing a polyT tail, such as 100T tail (size can be 50-5000 T), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines. The examples below demonstrate that a 100 base pair stretch of poly(A) is sufficient to enable efficient translation of an RNA transcript.

Poly(A) tails of RNAs can be further extended following in vitro transcription with the use of a poly(A) polymerase, such as E. coli polyA polymerase (E-PAP). The examples below demonstrate that increasing the length of a poly(A) tail from 100 nucleotides to between 300 and 400 nucleotides results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA. Suitable ATP analogs include, but are not limited to, cordiocipin and 8-azaadenosine (FIG. 2B).

5' caps on also provide stability to RNA molecules. In a preferred embodiment, RNAs produced by the methods disclosed herein include a 5' cap. The 5' cap may, for example, be $m^7G(5')ppp(5')G$, $m^7G(5')ppp(5')A$, $G(5')ppp(5')G$ or $G(5')ppp(5')A$ cap analogs, which are all commercially available. The 5' cap can also be an anti-reverse-cap-analog (ARCA) (FIG. 2B and also Stepinski, et al., *RNA*, 7:1468-95 (2001)) or any other suitable analog. The 5' cap is provided using techniques known in the art and described herein (Cougot, et al., *Trends in Biochem. Sci.*, 29:436-444 (2001); Stepinski, et al., *RNA*, 7:1468-95 (2001); Elango, et al., *Biochim. Biophys. Res. Commun.*, 330:958-966 (2005)).

The RNAs produced by the methods disclosed herein can also contain an internal ribosome entry site (IRES) sequence. The IRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included.

III. Methods of Use

A. Introduction of RNA into Target Cells

RNA can be introduced into target cells using different methods, for instance, commercially available methods which include, but are not limited to, electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany), cationic liposorne mediated transfection using lipofection, polymer encapsulation, peptide mediated transfection, or biolistic particle delivery systems such as "gene guns" (see, for example, Nishikawa, et al. *Hum Gene Ther.*, 12(8):861-70 (2001).

B. Applications

The mRNA construct can be delivered into different types of eukaryotic cells as well as into tissues and whole organisms using transfected cells as carriers or cell-free local or systemic delivery of encapsulated, bound or naked mRNA. The method can be used for any purpose where a transient expression is required or sufficient.

The disclosed method can be applied to modulation of cell activity in basic research and therapy, in the fields of cancer, stem cells, acute and chronic infections, and autoimmune diseases, including modulation of the developmental pathways.

Cells suitable for use with the disclosed method include, but are not limited to, primary cells and established cell lines, embryonic cells, immune cells, stem cells, and differentiated cells such as fibroblasts, hematopoietic, and epithelial cells. The disclosed method can be used for functional modification of different types of cells including, but not limited to, such cells as fibroblasts, hematopoietic and epithelial cells, to convert them into different types of stem cells (including embryonic stem cells), without permanent alteration of cell genomes.

Because of the high efficiency of transfection, typically more than 90% of the cell population, it is possible to transfect cells with multiple distinct mRNAs or a mixture of mRNAs and small interfering RNA's (siRNA) simultaneously. For example, it is possible to generate an autologous lymphocyte population with multiple sets of receptors to recognize and destroy targets which otherwise escape cytotoxic T lymphocyte (CTL) surveillance or to increase the specificity of the CTL towards selected targets. Similar procedures could be used with NK or NKT cells or other types of immune effector cells to target them to specific cells or tissues or increase their avidity for specific cells or tissues. The method can also be used to introduce various mRNAs and/or siRNAs that render the T cell resistant to inhibitory molecules in vivo. Also, mRNAs that encode transcription factors and/or effector proteins characteristic of $CD8^+$ cytotoxic T cells can be introduced into a mixed population of T lymphocytes in order to convert them all to a cytotoxic T cell phenotype.

This method also provides the ability to control the level of expression over a wide range by changing the amount of input RNA, making it possible to individually regulate the expression level of each transfected gene. Furthermore, the PCR-based technique of mRNA production highly facilitates the design of the chimeric receptor mRNAs with different structures and combination of their domains. For example, varying of different intracellular effector/costimulator domains on multiple chimeric receptors in the same cell allows determination of the structure of the receptor combinations which assess the highest level of cytotoxicity against multi-antigenic targets, and at the same time lowest cytotoxicity toward normal cells.

1. Immunomodulation

Genetic transduction of different types of cytotoxic lymphocytes to express desired receptors for adoptive immunotherapy is a valuable method to redirect the specificity of lymphocytes for tumor antigens, which are not readily recognized by the endogenous αβ T-cell or NK receptors. However, a potential disadvantage of such method is genome integration of transgenes as well as the technical complexity of the method. It takes weeks or months to clone and accumulate a desirable homogeneous specific lymphocyte population suitable for the treatment. Another problem of cloning is that lymphocyte diversity, an important factor which determines immune response, is an unavoidable complication of such procedure. Cytotoxic lymphocytes are presented as heterogeneous subpopulations such as CD8+, CD4+, CD3+ CD56+(CIK) T cells and CD3– CD56+ NK cells, with additional sub diversity among each of subpopulation. The whole cytotoxic potential can be influenced by cooperation of different cell types. The RNA transfection is essentially transient and a vector-free: mRNA transgene can be delivered and expressed into the lymphocytes after brief in vitro cell activation, as a minimal expressing cassette without any additional viral sequences. In these conditions genome integration of the transgene is quite improbable. Cell cloning becomes unnecessary because of the efficiency of mRNA transfection and its ability to uniformly modify the entire lymphocyte population. Moreover, different types of lymphocytes such as CD3+ CD8+, CD3+ CD4+ T cells and Cd56+ CIK and NK cells can be simultaneously transfected with CIR mRNA and used together to increase their potential synergistic effect. Thus, cells containing an RNA construct introduced according to the disclosed method can be used therapeutically. For example, a lymphocyte cell population could be withdrawn from a patient, transfected with different RNA constructs, and then reintroduced into the patient. The transfected cell population would then target lymphoma or other cancer cells, which contain the CD19 or other target antigen. A benefit of the use of mRNA transfected cells is that mRNA transgene has a limited half-life. The encoded protein will only be produced by the transfected cell for a limited period of time. This may reduce unintended consequences when genetically modified cells are reintroduced into a patient.

In the preferred embodiment, the technology is used for personalized therapy. For example, for treatment of tumors, the patient's blood or cells would be collected by an appropriate method such as apheresis, biopsy or venapuncture. The cells would be cultured for at least 24 hours during which time the cells are transfected with an appropriate construct to treat the tumor. The cells can be stored frozen before transfection, if necessary. These are then returned and administered back to the patient.

In other applications, the method can use an appropriate construct to de-differentiate cells, for example, converting adult cells into stem cells, using genes described in the literature. See, for example, Yu, et al., *Science,* 318:917-1920 (2007) and Yamanaka, *Cell Prolif,* 41-51 (2008). The method can also be widely used for transient reprogramming of cells, for example, modulation of cell metabolism and differentiation.

EXAMPLES

Material and Methods

Cells

*Escherichia coli* cells were grown on LB broth with 100 µg/ml ampicillin

Mouse; EML cells were grown on Iscove's Medium (Gibco) supplemented with 20% Donor Horse serum with BHK conditioned media and non-essential amino acids.

Human Cell Lines

Hela and Human Non-Hodgkin's B cell Lymphoma line CRL2261 cells were grown on DMEM (GIBCO) supplemented with 10% fetal bovine serum (FBS), glutamate. Bjab, BL2, Palo, NB4, Jurkat cells were grown in RPMI Medium supplemented with 10% FBS.

Primary Human Cells

Activated B cells were received by cultivating mononuclear cells (MNC) in the presence of CD40 ligand activation as described by Schultze, et al., *Proc. Natl. Acad. Sci.,* 92:8200-8204 (1995). MNCs were washed and plated on pre-formed layer of previously irradiated (96Gy) 3T3-CD40L on IMDM (Gibco), with 10% human serum (Gemini Bio-Products, CA, USA), 200 U/ml IL-4 and in the presence of Cyclosporin A (Sigma). The cultured B-cells were transferred in new pre-layered plates and re-stimulated every 3-4 days. Cultures were kept up to 21 days. The percentage of CCD19-positive cells was 85-95% after day 10 of cultivation.

Populations of activated CD3+ cells were obtained from MNCs using XCYTE DYNABELADS® (Xcyte Therapies) with covalently attached anti-CD3 and anti-CD28 monoclonal antibodies. MNCs were resuspended at $10 \times 10^6$/ml in DPBS, 0.5% HA and XCYTE DYNABEADS® (50 µl per ml of sample) were added. The mixture then was incubated 30 min in a refrigerator with rotation. The positive (CD3+) fraction was isolated by Dynal MPC and cultivated 7-10 days in IMDM (Gibco), with 5% human serum (Gemini Bio-Products), in the presence of 100 IU/ml Interleukin-2 (PeproTech, NJ, USA). The beads were removed from the culture before electroporation.

CD8+ cells were isolated from CD3+ cells by Cd8+ T Cell Isolation Kit II (Miltenyi Biotec, Germany) according to the manufacturer's recommendations. The purity of selected CD8+ cells was 96%.

Reagents: Yeast tRNA and DNA ladders were purchased from Invitrogen, 8-azaadenosine-5'-triphosphate and cordiocipin—from TrfiLink Biotechnologies, polyadenilic acid—from MP Biomedicals.

RNA Synthesis mRNA constructs based on the Pontelina plumata green fluorescent protein ("GFP") sequence of pmaxGFP plasmid (Amaxa Biosystems) were produced in vitro using T7 RNA polymerase (RNAP). Forward primer contained T7 RNA P promoter and anchoring sequence to the proximal part of the GFP expression cassette. Reverse primer with anchoring sequence to distal part of GFP expression cassette contained a stretch of 100 oligo-dT. mRNA synthesis was provided with mMESSAGE Mmashine® kit (Ambion), using the procedure recommended by the manufacturer. In some cases the product was additionally polyadenylated using the reagent of the same kit. The final product was treated with DNaseI and purified by Ambion MEGAclear kit or by LiCl precipitation.

Transfections

Electroporation was performed using an Amaxa NUCLEOFECTOR™-II (Amaxa Biosystems, Cologne, Germany) in accordance with manufacturer recommendations. Jurkat and B cell lines were transfected using NUCLEOFECTOR™-II solution V and the set of recommended regimes for electroporation. EML cells were transfected using solutions V, T and R and different regimes of electroporation. T lymphocytes were transfected using T cell NUCLEOFECTOR™-II solution and different regimes of electroporation. Alternative methods of nucleic acids delivery were also used: cationic liposome mediated transfection was performed using LIPOFECTIN or LIPOFECTAMIN (Invitrogen). Electroporation was also performed with the ECM 830 (BTX) (Harvard Instruments, Boston, Mass.) or the Gene Pulser II (BioRad, Denver, Colo.), Multiporator (Eppendorf, Hamburg Germany). All procedures were performed as directed by the manufacturers. pmaxGFP plasmid DNA (Amaxa Biosystems) was used as the DNA control. The efficiency of transfection (ET) was determined 18 h after transfection by fluorescence activated cell sorting (FACS). In some experiments transfectants were further analyzed each 24 h until GFP could not longer be detected. Cell viability was determined by trypan blue dye exclusion.

Flow Cytometry

Flow cytometry was performed using the fluorescent activated cell sorting (FACS®) assay. Flow cytometry was performed on cell subpopulations was performed at the Yale Cancer Center Flow Cytometry Shared Resource, using a FACS® Calibur flow cytometer (Becton-Dickinson, San Jose, Calif.) equipped with 488 nm laser and the standard filter setup. Fluorescence signals were collected on a logarithmic scale. A minimum of ten thousand cells were interrogated for each sample. Analysis of data was performed using FlowJo software (Tree Star, Inc., San Carlos, Calif.). The expression efficiency was calculated as the difference between the geometric mean of fluorescence of the transfectants and control (mock transfected) cells. Mouse anti-human CD4 FITC (anti-CD4 antibody, fluorescein isothiocyanate conjugated), CD8 PE (anti CD8 antibody, phycoerythrin conjugated, CD19PE (anti-CD19, PE conjugated), and CD3 PerCP-Cy5.5 (anti-CD3 antibody, peridinin chlorophyll protein [PerCP]-Cy5.5 conjugated), were purchased from BD Biosciences Pharmingen (San Diego, Calif.), Streptavidin-PerCP (streptavidin, PerCP conjugated)—from BD Immunocytometry Systems (Philadelphia, Pa.), and Biotin-conjugated goat anti-mouse IgG was from Jackson ImmunoResearch Laboratories (West Grove, Pa.). Cells were stained according to the manufacturer's recommendation.

Electrophoresis:

DNA samples were run in 1% agarose in Tris-acetate buffer, 2 v/cm RNA samples were run in 1% agarose in MOPS-formaldehyde buffer, 2 v/cm, using RNA Millenium marker (Invitrogen) as size standard.

Cytotoxicity Assay

The cytotoxic activity of electroporated CD3+ CD8+ cells were evaluated by a standard $^{51}$Cr release method. CRL2261 and lymphoblastoid B cells were used as targets. The target B cells, CRL2261 and K562 cells were labeled with 0.25 mCi of $^{51}$Cr-sodium chromate (MP Biomedicals, Inc., Irvine, Calif., USA) for 1 hour, extensively washed and seeded at a density of 10×104 in V-bottom 96 well microplates. Transfected CD8+ CD3+ effector (E) cells were suspended in IMDM (Gibco), 10% FBS medium and added to target cells at different E:T ratios. The plates were incubated at 37° C. for 4 h, and aliquotes of each sample were harvested for gamma counting in order to assess 51Cr release. Calculations were carried out in triplicate. Specific lysis was calculated as lysis $$\% = \frac{\text{Observed release}(c.p.m) - \text{spontaneous release}(c.p.m)}{\text{Total release}(c.p.m) - \text{spontaneous release}(c.p.m)} \times 100$$

where c.p.m. is the count/min released by targets incubated with effector cells. Spontaneous release was determined from wells to which 100 µl of complete medium was added instead of effector cells. Total releasable radioactivity was measured after treating the targets with 100 µl of 1% Tritob X100.

Xenograft Tumor Model

On day 0, 6 week-old female NOD/Scid (NOD/LtSz-Prkdc Scid/J) mice (Jackson Laboratory) were injected in the peritoneum with 3×10$^6$ ffLuc+Daudi cells. On days 2 and 3 tumor engraftment was evaluated by biophotonic imaging. Mice with progressively growing tumors were segregated into 3 treatment groups (8 mice per group) receiving additional intraperitoneal (ip) injection of RPMI medium (medium control) (Group 1) or 5×10$^6$ CTLs: mock transfected CTLs (Group 2) or anti-CD19 CIR mRNA transfected CTLs (Group 3).

Biophotonic Tumor Imaging

Anesthetized mice were imaged using Xenogen IVIS 100 system beginning 15 minutes after ip injection of 150 ml of a freshly thawed aqueous solution of D-luciferin (Xenogen, Alameda, Calif.). Each animal was serially imaged in an anterior-posterior orientation at the same relative time point after D-luciferin injection. Photons emitted from ffLuc Daudi xenografts were quantified using the software program Living Image (Xenogen), and the bioluminescence signal was measured as total photon flux normalized for exposure time and surface area and expressed in units of photons (p) per second per cm2 per steradian (sr). For anatomic localization, a pseudocolor image representing light intensity (blue, least intense; red, most intense) was superimposed over a digital grayscale body-surface reference image.

Statistical Methods to Analyze Biophotonic Data

To measure the differences between mouse treatment groups, we considered evaluating tumor biophotonic signal over time, The signals were normalized for the initial values on day 3 after tumor injection (also the day of first CTLs injection) which was taken as 1 for each mouse. Data obtained for each group were presented as geometrical mean+/- geometrical SD.

The present invention will be further understood by reference to the following non-limiting examples.

Example 1

DNA Transfection in EML Cells

EML cells are a murine cell line that grows in suspension and has the capacity to differentiate into cells of several hematopoietic lineage in vitro. These cells would be of considerable interest for manipulation in vitro, but, unfortunately, they are relatively resistant to standard transfection methods. EML cells were therefore used as a model for exploring various DNA and RNA transfection methods with difficult cells. For convenience of assaying, a DNA plasmid expressing green fluorescent protein (GFP) was used. The following transfection methods were tested: lipofectin and Lipofectamin Lipofection, electroporation using square wave BTX ECM 830 apparatus or Bio-Rad Gene Pulser II, exponential diminishing wave electroporation using Eppendorf Multiporator, and also Amaxa nucleofector. All methods were optimized according to the recommendations of the manufacturers. The Amaxa nucleofection protocol gave the highest efficiency of transfection. The Amaxa procedure was optimized using different combinations of one of three solutions (V, R, and T) and 8 programs of electroporation.

The best result that could be obtained for plasmid DNA transfection was that 12% of the initial cells showing GFP expression, with slightly less than half the initial cells remaining viable after electroporation. Therefore 25% of the surviving cells expressed GFP under these conditions. Further optimization using the programs recommended by the manufacturer was not effective.

The DNA template was designed from the GFP sequence of the pmaxGFP plasmid. To avoid aberrant transcription of PCR-made DNA templates, a T7 promoter and 3' transcription terminator was introduced in the DNA template directly during PCR. The forward PCR primer contained a T7 RNA polymerase promoter and an anchoring sequence from the 5' untranslated region (5' UNR) of the GFP gene, The reverse primer needed a structure that allowed the correct transcriptional termination (FIGS. 1, 2A). The PCR product was used for in vitro transcription by T7 RNA polymerase purified and delivered into mouse EML cells by nucleofection pmaxGFP plasmid DNA was used as a control.

Effect of the 5' and 3' UTRs on Expression

GFP mRNA with short UTRs: 6 nucleotides upstream of ATG codon and 35 nucleotides downstream of stop codon, was virtually unexpressed. mRNA which included 44 nucleotides upstream of the ATG codon, and 113 nucleotides downstream of the stop codon, were efficiently expressed (Table 2).

TABLE 2

Transfectability of the GFP mRNA constructs

| Coordinates of ends of DNA matrix for mRNA synthesis | | |
|---|---|---|
| Left end Distance from first GFP codon (b) | Right end Distance from last GFP codon | Transfectability of GFP mRNA |
| −6 | +11 | − |
| −6 | +113 | − |
| −44 | +11 | − |
| −44 | +113 | + |
| −44 | +122 | + |

Effect of the 5'-Cap on the mRNA

It is well known that capping highly increases the efficiency of mRNA translation (Cougot et al., *Trends Biochem. Sci.*, 29:436-444 (2004); Pestova et al., *Proc. Natl. Acad. Sci.*, 98:7029-36 (2001)). The standard $m^7G(5')ppp(5')G$ in vitro capping analog can be incorporated in two orientations, therefore only one half of the mRNA product is active. Recently, Ambion and others introduced a new anti-reverse-cap-analog (ARCA) (Stepinski et al., *RNA*, 7:1486-95 (2001)), which lacks one of the 3'OH groups and can be incorporated in mRNA only in the correct orientation.

Using ARCA, a two-fold increase of GFP expression compared to the standard capping procedure was obtained, as demonstrated by (FIG. 2B).

Effect of the mRNA 3' Poly (A) Tail Length

There are two basic methods of construction of a poly(A) tail: insertion of a terminal poly(A/T) segment into the DNA template or direct addition of poly(A) residues to the RNA transcripts by a poly(A) polymerase. In these studies, a 3' terminal poly(A/T) stretch introduced by PCR with a reverse primer containing 100 b of poly(T) was sufficient for mRNA expression. However, posttranscriptional RNA polyadenylation by *E. coli* poly(A) polymerase (E-PAP), which expanded the poly(A) tail from 100 up to 300-400 nucleotides, resulted in an additional two-fold increase in expression. The expression could also be increased without tail extension when the ATP in the E-PAP reaction was replaced by modified ATP analogs: cordycepin or 8-azaadenosine (FIG. 2B). The stimulation of expression by poly(A) extension or by the insertion of ATP analogs probably provided better mRNA protection from 3'-exonuclease degradation. GFP expression was not affected by an excess of yeast tRNA, but was inhibited by an excess of free polyadenylate (FIG. 2B).

An optimized GFP mRNA construct contained 44b and 113b flanking UTR sequences, an ARCA cap, and a 300-400 b polyadenylate tail. The efficiency of mRNA and DNA transfection had the same pattern of dependence on the electroporation programs used: increasing strength of electroporation resulted in increasing the intensity of GFP expression for DNA and mRNA samples and decreasing of cell viability. Therefore the same nucleofector programs were effective for both DNA and RNA electroporation. After DNA electroporation using the most efficient program-T01, only one fourth of the EML cells were transfected, and these showed highly heterogeneous levels of expression. After mRNA electroporation, almost all cells appeared as a population uniformly expressing GFP. The level of GFP expression caused by plasmid DNA as well as by mRNA in EML cells was highest the day after transfection, and decreased to zero in 4 days (FIG. 3A).

The optimized mRNA construct was used to transfect different human cell lines. Nucleofector programs for each cell line were chosen in accordance with Amaxa cell line protocols. FACS analysis was conducted for EML and Jurcatt cells transfected with green fluorescent protein ("GFP") mRNA: 6, 17, 50 and 150 mg mRNA/ml and 10 mg DNA/ml.

In all experiments mRNA transfected almost all of the cells, and resulted in highly efficient and uniform gene expression as shown in FIGS. 3A and 3B. Efficiency of transfection measured as the difference between mRNA transfected and mock transfected cell fluorescence.

TABLE 3

Efficiency of transfection measured as the difference between mRNA transfected and mock transfected cell fluorescence.

| | mRNA (mg/ml) | | | | DNA (mg/ml) |
|---|---|---|---|---|---|
| | 6 | 17 | 50 | 150 | 10 |
| EML | 3.9% | 54.4% | 89.8% | 95% | 27.4% |
| Jurkat | 88.8% | 96.2% | 97.1% | 97.0% | 81.4% |

Human cells can sustain OFP expression caused by plasmid DNA as well as by mRNA for a longer time than mouse EML cells, up to 10 days, as shown in FIG. 3B. Efficiency of transfection for different human cells calculated as the geometric mean fluorescence of the transfected population, showed striking superiority of mRNA expression to that of DNA Relatively long term GFP expression was also observed in the human B cell lines Bjab, BL2 and Palo.

Plasmid DNA was toxic for the cells in a concentration of more than 20 μg/ml. In contrast, no toxicity of GFP mRNA was observed even when it was used at concentrations of more than 150 μg/ml (FIG. 3C).

Example 2

Transfection of Human Primary T Lymphocytes

The method of OFP mRNA synthesis was used to produce the mRNA of the human chimeric anti-CD19 receptor. This receptor contains a leader sequence, an antiCD19 single strand antibody domain, a transmembrane domain and two intracellular signal transduction domains: a 4-1DBB and a CD3 zeta, as shown in FIG. 4. Cloned in the appropriate integrative DNA vector, the receptor is able to redirect transfected CD8+ lymphocytes as well as natural killer cells toward the CD19+ targets (Imai at al., *Leukemia*, 18, 676-684 (2004); Imai et al., *Blood*, 106:376-383 (2005). The plasmid pMSCV-IRES-antiCD19-BB-zeta was used as a template to produce the receptor mRNA. The product included the coding sequence, the 50 b 5'UTP, and the 84 b 3'UTP with an extended 400b polyA tail.

Jurkat cells transfected with this mRNA expressed receptor on their surface. Simultaneous transfection of the cells with the receptor and GFP mRNAs showed that both mRNAs can be delivered and expressed without interference. Double mRNA transfection occurred with the same pattern and efficiency as the transfection with single mRNA and was detected in more then 90% of cell population.

Using pmaxGFP plasmid DNA, the transfection procedure for primary human T lymphocytes was optimized. The standard Amaxa Biosystems protocol for activated primary T cells recommends programs T20 and T23. However, these programs resulted in low viability of the cells. The protocol was optimized and better results were obtained with programs T3 and T7, which gave a relatively low but substantial level of pmaxGFP transfection with high viability (greater than 90%). When transfected with receptor mRNA, more than 80% of the CD3+ T lymphocytes expressed the receptor on their surface. Both the CD4+ and the CD8+ subpopulation were equally transfectable and showed the same kinetics of mRNA expression (FIG. 5).

Example 3

Transfection of CD3+ T Lymphocytes with Anti-CD19-CIR mRNA

Cells were transfected with anti-CD19-CIR mRNA (40 μg/ml) and analyzed by FACS. Cells were labeled with antibody specific to anti-CD19-CIR, CD8, and CD4. Anti-CD19-CIR expression efficiency was calculated as the difference between geometric means of fluorescence of the transfectants and control (mock-transfected) cells. The fluorescence value of mock-transfected cells was measured as approximately 3 units (negative control). Therefore 63 units of total fluorescence corresponded to a 60-unit increase in fluorescence relative to the control. Both the CD4+ and CD8+ subpopulations were equally transfectable, possessed the same pattern of mRNA expression, and were able to sustain anti-CD19-CIR expression for at least 3 days (FIG. 5).

Example 4

Cytotoxicity of CD8+ T Lymphocytes Transfected with Various Amounts of Anti-CD19-CIR mRNA CD8+ T lymphocytes (CTLs) were transfected with various amounts of anti-CD19-CIR mRNA. Cells were mock transfected or transfected with anti-CD19-CIR mRNA at 13.3 μg/ml, 40 μg/ml, or 120 μg/ml. (a) FACS analysis of transfectants demonstrating various levels of anti-CD19-CIR expression. The same transfectants were analyzed for cytotoxicity with different targets at the indicated E:T ratio. T lymphocytes were incubated for 4 hr with different target cells, loaded with 51Cr: autologous cells (FIG. 6A); allogeneic CD19+ B lymphoblasts (FIG. 6B); CD19-K562 cells (FIG. 6C).

CD8+ T lymphocytes transfected with anti-CD19-CIR mRNA specifically killed CD19+ targets, whereas mock-transfected control lymphocytes were not cytotoxic. The CD19-negative target cell line K562 was resistant to receptor-mediated killing (FIG. 6). Of note, even the minimal level of receptor expression detectable by FACS analysis was sufficient for target cell killing (FIG. 6). This result was reproduced with lymphocytes from three different donors.

The experiments above demonstrate that human lymphocytes can be transfected with anti-CD19 CIR mRNAs with high efficiency. After transfection virtually the whole cell populations uniformly expressed chimeric receptors and possessed cytotoxicity against allogeneic and autologous B cells. The expression of the receptor on the surface of lymphocytes was detected for at least 3 days after transfection (FIG. 5). Even the minimal detectable level of receptor expression was sufficient for cytotoxicity. The results in FIG. 5 demonstrate that transfected cytotoxic T lymphocytes (CTLs) can sustain their cytotoxicity for at least several days.

Example 5

Cytotoxicity of CD8+ T Lymphocytes Transfected with Anti-CD19 Chimeric Receptor mRNA Against Different CD19+ Tumor Cells In a $^{51}Cr$ assay, it was observed CIR-specific lysis of all CD19+ targets tested, including Daudi lymphoma and NALM6 leukemia cell lines, as well as autologous B lymphoblastoid cells, whereas mock-transfected control lymphocytes were not cytotoxic. The CD19-negative target cell line K562 was resistant to receptor-mediated killing (FIG. 7).

Example 6

Effect of Lymphocyte Activation on mRNA Transfection

The necessity of lymphocyte activation for mRNA transfection was analyzed. Because nucleofector program efficiencies were similar for both DNA and RNA electroporation (US, Amaxa), lymphocyte transfectability was determined using transient transfection with a GFP plasmid DNA. CD3+ CD8+ lymphocytes taken without activation were electroporated with GFPmax plasmid DNA using the following different programs recommended by Amaxa for these cells: T7, T13, T20, U1, U8, U10, U5, U14, U9.

The T7 program was chosen for the next step. CD3+ CD8+ lymphocytes were incubated 1 or 7 days with CD3-CD28 beads and IL2 and then transfected with anti-CD19 CIR mRNA.

Non-activated CD3+ CD8+ cells were virtually untransfectable: less then 2% of the whole population showed green fluorescence determined by expression of GFP transgene. CD3+ CD8+ lymphocytes activated by 7 day incubation with CD3-CD28 beads and IL2 showed normal level of transfectability—up to 40% of the cells expressed GFP for programs T13 and T7, with correspondent viability 40 and 55%.

Both samples were transfected using the T7 program with similar efficiency, and possessed the same level of cytotoxicity against CD 19+ targets, as demonstrated by FIGS. 8B-8D. Therefore, CD8+ lymphocyte activation is essential for CIR mRNA transfection and one day of cell incubation with Cd3-CD29 beads and IL2 is sufficient for CTL activation.

The presence of two signaling domains in the cytoplasmic part of CIR facilitates lymphocyte proliferation. However it was not clear if their activity can produce synergistic effects on receptor-mediated cytotoxicity. To investigate this, the 4-1BB signaling part of the anti-CD19 CIR was deleted by a 3-step PCR. This construct was transcribed into mRNA and compared with the original RNA. Both original CIR mRNA and the CIR mRNA construct with 4-1BB deletion transfected CTLs with similar efficiency, and generated a similar level of cytotoxicity against CD19+ targets (FIG. 8B). Thus, in short run experiments where lymphocyte proliferation is not very important, the presence of the zeta subunit as a sole cytoplasmic domain in CIR is sufficient.

Example 7

Modulation Different Types of Lymphocytes with Anti-CD19 CIR mRNA

The killing efficiency of NK cells stably transfected with CD19 CIR has been previously demonstrated by Imai, et al., *Leukemia*, 18:676-684 (2004) using retroviral transduction. The ability to transfect NK cells as well as T cells from the same donor with CD19CIR mRNA was tested. Efficiency of electroporation depends on the source of lymphocytes, and electroporation should be optimized for each donor. Also, NK cells electroporation is often less efficient then electroporation of T cells (Amaxa).

Electroporation was optimized using cells obtained from a single donor. CD3+ T cells (CD4+ and CD8+) as well as CD56+ cells (CD3+ CD56+CIK and CD3− CD56+ NK cells)

were transfected with GFP transgene. T7 Amaxa program with a T cell Amaxa kit was efficient for both cell groups and chosen for farther experiments. Three subpopulations: CD3+ CD8+, CD3+ CD4+ T cells and CD3⁻ CD56+ NK cells were separated, electroporated with anti-CD19 CIR mRNA and tested for cell cytotoxicity toward autologous B cells. The lymphocytes subpopulations: CD8+, CD4+ T cells and a mixture of CD8+ and CD4+ cells (in a 1:1 ratio) as well as NK cells were transfected with anti-CD19 CIR mRNA. Target cells were loaded with $^{51}$Cr and analyzed for cytotoxicity. At the E:T ratios shown in FIG. 9, all cell populations expressing the anti-CD19 chimeric receptor were cytotoxic. These studies demonstrate that there is no need to separate any specific type of cytotoxic cells in order to increase the efficiency killing target cells; rather the entire lymphocyte population could be used for mRNA CIR transfection.

Example 8

Lymphocyte Reprogramming Against K562, Melanoma and Myeloma Cells

Solid tumor cells usually do not express CD19. CD9 negative A2058 melanoma and RPMI8126 myeloma cell lines, and also K562 cells, were transfected with CD19 receptor mRNA and used as a targets. The CD19 gene was obtained from ORIGEN, transcribed in vitro and then the mRNA introduced by electroporation in A 2058 and K562 cells. Next day the whole population of target cells uniformly expressed the CD19 and was loaded with $^{51}$Cr and used as target for CD8+ CTLs transfected with anti-CD19 CIR mRNA. Anti-CD19 CIR+ CTLs were able to kill transfected CD19+ melanoma and k562 cells, but possessed low or no cytotoxicity against non-transfected, targets (FIGS. 10A and 10B). A similar result was obtained with RPMI8126 myeloma cells used as a target (FIG. 11).

Example 9

Lymphocyte Reprogramming Against Solid Tumor Cells Using 8H9CIR

Another chimeric receptor which is made with the 8H9 antibody against a gp58 antigen protein often expressed on different tumor lines (Cheung et al., *Hybridoma and Hybridomics*, 22:209-218 (2003)) (see FIG. 12A) was introduced into human CTLs.

Transfected lymphocytes killed all different solid tumor cells, such as primary melanoma, breast ductal carcinoma, rhabdosarcoma and breast adenacarcinoma which express the correspondent cancer antigen on their surface (FIGS. 12C-12F). Antigen negative K562 cells were resistant to such killing (FIG. 12B).

Example 10

Cytotoxic Activity of Anti-CD19 CIR+ CTLs In Vivo

A xenogenic mice model for lymphocyte therapy of Daudi lymphoma described by Kowolik, et al., *Cancer Res.*, 66(22): 10995-1004 (2006) was used, 9 none-obese diabetic/severe combined immunodeficiency (NOD/Scid) mice were divided into 3 groups. Each group was ip injected with either 1×10⁶, 3×10⁶ or 9×10⁶ ffLuck Daudi cells per mouse and analysed by biophotonic measurements Exponentially growing tumors were established in all mice 3 days after injection. In an initial experiment 6 mice were ip injected with 3×10⁶ ffLuc+ Daudi cells and 3 days later therapy with human CTLs was initiated. Because the receptor stays on the CTL surface for about 3-4 days, the mice were injected with 5×10⁶ CTLs per mice every third day. Half of the mice were injected twice on day 3 and day 6 after ffLuck Daudi lymphoma introduction, with mock CTLs (control) and the other half with anti-CD19 CIR mRNA modified CTLs. Treatment with modified cells resulted in marked regression of tumors, while in control group tumors continued to grow.

A larger experiment was then performed. 3×10⁶ fluc Daudi cells per mice were seeded into the peritoneum of 24 NOD/Scid mice. 3 days later mice were analyzed by biophotonic measurements and were divided into 3 groups (8 mice per group, with median ffLuc signal (~6×10⁸ p/s/cm²/sr), similar for each group. The mice were injected with 5×10⁶ CTLs per mouse every third day and were given CTLs injections three times on days 3, 6 and 9. The mice were imaged on days 3, 6, 9, 12 and 15. Compared with tumor-bearing control mice given RMPI medium alone (group 1) and mock transfected CTLs (group 2), there was significant reduction of tumor ffLuc signal in mice given anti-CD19 CIR mRNA transfected CTLs (group 3) (FIG. 13).

Pseudocolor image representing light intensity and anatomic localization of the ffLuc-Daudi cells in three representative mice and longitudinal monitoring of the bioluminescent signals of ffLuc+ Daudi cells (FIG. 13) show that tumor growth inhibition was still evident 3 days after the last CTLs injection on day 12. For each group of mice the biophotonic signal outcome was normalized by the initial values at the beginning of CTL-mediated treatment. Geometric means of the signal was used for presentation based on the assumption of the lognormal distribution for the sizes of the tumors (Spratt, *J. Surgical Research*, 9:151-157 (1969)).

Modifications and variations will be obvious to those skilled in the art and are intended to come within the scope of the appended claims.

We claim:

1. A linear double-stranded DNA template obtained by Polymerase Chain Reaction (PCR) and suitable for in vitro transcription of an mRNA comprising from 5' to 3':
   an RNA polymerase promoter on the coding strand of the double-stranded DNA,
   a 5' untranslated region less than 3,000 nucleotides in length and effective for translation of the mRNA into a detectable polypeptide after transfection into a eukaryotic cell,
   an open reading frame that encodes the polypeptide, wherein the polypeptide is heterologous to the cell to be transfected and wherein the polypeptide is selected from the group consisting of a ligand or a receptor of an immune cell, a polypeptide that stimulates or inhibits a function of the immune system, and a polypeptide that inhibits the function of an oncogenic polypeptide,
   3' untranslated region of the mRNA into a detectable polypeptide after transfection into a eukaryotic cell, and
   a poly(A) stretch of 50-5,000 nucleotides on the coding strand of the double-stranded DNA,
   wherein the promoter is heterologous to the open reading frame, and
   wherein the DNA template is not contained within a DNA vector and terminates with the 3' end of the poly(A) stretch.

2. The linear double-stranded DNA template of claim 1 wherein the RNA polymerase promoter comprises a consensus binding sequence for an RNA polymerase selected from the group consisting of T7, T3 or SP6 RNA polymerase.

3. The linear double-stranded DNA template of claim 1 wherein the open reading frame encodes a fusion polypeptide.

4. The linear double-stranded DNA template of claim 1 wherein the open reading frame encodes a polypeptide that is a ligand or receptor for an immune cell.

5. The linear double-stranded DNA template of claim 1 further comprising an internal ribosome entry site.

6. A method of generating the linear double-stranded DNA template of claim 1 comprising
   generating forward and reverse primers,
   wherein the forward primer comprises a plurality of nucleotides that are substantially complementary to the non-coding strand of a target double-stranded DNA of interest, and a plurality of nucleotides that function as a binding site for an RNA polymerase,
   wherein the reverse primer comprises a plurality of nucleotides that are substantially complementary to the coding strand of a target double-stranded DNA of interest, and a plurality of deoxythymidine nucleotides, and
   performing polymerase chain reaction amplification of the target DNA using the forward and reverse primers to form the linear double-stranded DNA template of claim 1.

7. A method of generating the linear double-stranded DNA template of claim 1 comprising
   generating forward and reverse primers,
   wherein the forward primer comprises a plurality of nucleotides that are substantially complementary to a region of nucleotides directly upstream of a target double-stranded DNA of interest,
   wherein the reverse primer comprises a plurality of nucleotides that are substantially complementary to a region of nucleotides directly downstream of a target double-stranded DNA of interest, and
   performing polymerase chain reaction amplification of the target DNA using the forward and reverse primers to form the linear double-stranded DNA template of claim 1.

8. The method of claim 6 or 7 wherein the primers comprise nucleotide sequences that are substantially complementary to stretches of nucleotides in the 5' and 3' untranslated regions of a double-stranded DNA of interest.

9. The method of claim 6 or 7 wherein the primers comprise nucleotide sequences that are substantially complementary to stretches of nucleotides within the open reading frame of a double-stranded DNA of interest.

10. The method of claim 6 wherein the primers comprise nucleotide sequences that are substantially complementary to stretches of nucleotides within the open reading frame of a double-stranded DNA of interest, wherein the primers further comprise stretches of nucleotides that comprise 5' and 3' untranslated regions, wherein the stretch of nucleotides in the forward primer that comprise the 5' untranslated region is between the nucleotides that comprise the RNA polymerase promoter and the nucleotides that are substantially complementary to the non-coding strand of a target double-stranded DNA of interest, and wherein the stretch of nucleotides in the reverse primer that comprise the 3' untranslated region is between the plurality of deoxythymidine nucleotides and the nucleotides that are substantially complementary to the coding strand of a target double-stranded DNA of interest.

11. The method of claim 6 wherein the forward primer and open reading frame comprises a consensus Kozak sequence.

12. A method of generating one or more RNAs for transfection of cells comprising performing in vitro transcription from the linear double-stranded DNA template of claim 1.

13. The method of claim 12 further comprising using a poly(A) polymerase to extend the poly(A) tail of the RNA with one or more adenine nucleotides or analogs thereof.

14. The method of claim 12 further comprising adding nucleotides during transcription that function as a 5' cap for the transcribed RNA.

15. One or more isolated RNAs comprising one or more open reading frames, produced by the method of claim 12.

16. A method for expressing one or more RNAs in a cell comprising contacting cells with one or more RNAs of claim 15.

17. The method of claim 16 for expressing more than one RNAs of claim 16, wherein the RNAs are present in unequal molar amounts to provide separate expression levels of the RNAs in the cells.

18. The linear double-stranded DNA template of claim 1, wherein the poly(A) stretch is 300-400 nucleotides in length.

19. The linear double-stranded DNA template of claim 1, wherein from 5' to 3' the template consists of an RNA polymerase promoter on the coding strand of the double-stranded DNA, a 5' untranslated region less than 3,000 nucleotides in length and effective for translation of the mRNA into a detectable polypeptide after transfection into a eukaryotic cell, an open reading frame that encodes the polypeptide, wherein the polypeptide is heterologous to the cell to be transfected and wherein the polypeptide is selected from the group consisting of a ligand or a receptor of an immune cell, a polypeptide that stimulates or inhibits a function of the immune system, and a polypeptide that inhibits the function of an oncogenic polypeptide, a 3' untranslated region effective for translation of the mRNA into a detectable polypeptide after transfection into a eukaryotic cell, and a poly(A) stretch of 50-5,000 nucleotides on the coding strand of the double-stranded DNA, wherein the promoter is heterologous to the open reading frame, and wherein the DNA template is not contained within a DNA vector and terminates with the 3' end of the poly(A) stretch.

20. The linear double-stranded DNA template of claim 19 wherein the 3' untranslated region is at least 100 nucleotides.

* * * * *

UNITED STATES PATENT AND TRADEMARK OFFICE
CERTIFICATE OF CORRECTION

PATENT NO. : 8,859,229 B2  
APPLICATION NO. : 12/025700  
DATED : October 14, 2014  
INVENTOR(S) : Peter M. Rabinovich et al.

Page 1 of 1

It is certified that error appears in the above-identified patent and that said Letters Patent is hereby corrected as shown below:

In the Claims

Claim 16, Column 25, Line 27, replace "cells with one or more" with --the cell with the one or more--.

Signed and Sealed this  
Second Day of July, 2019

Andrei Iancu  
*Director of the United States Patent and Trademark Office*

UNITED STATES PATENT AND TRADEMARK OFFICE
CERTIFICATE OF CORRECTION

PATENT NO. : 8,859,229 B2  
APPLICATION NO. : 12/025700  
DATED : October 14, 2014  
INVENTOR(S) : Peter M. Rabinovich et al.

It is certified that error appears in the above-identified patent and that said Letters Patent is hereby corrected as shown below:

In the Specification

Column 1, Lines 5-7, replace "The United States government has certain rights in this invention by virtue of NIH grant numbers N01-HV-28186, AA15632, DA13334, AA11197, and AA000171." with "This invention was made with government support under AA015632, DA013334, AA011197 and HV028186 awarded by National Institutes of Health. The government has certain rights in the invention."

Signed and Sealed this  
Ninth Day of June, 2020

Andrei Iancu  
*Director of the United States Patent and Trademark Office*